United States Patent
Suresh et al.

(10) Patent No.: US 12,128,566 B2
(45) Date of Patent: Oct. 29, 2024

(54) GUIDED TOOL CHANGE

(71) Applicant: Intuitive Surgical Operations, Inc., Sunnyvale, CA (US)

(72) Inventors: Ashwinram Suresh, San Jose, CA (US); Lawton Verner, Saratoga, CA (US); Gabriel Brisson, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 401 days.

(21) Appl. No.: 17/438,377

(22) PCT Filed: Mar. 10, 2020

(86) PCT No.: PCT/US2020/021908
§ 371 (c)(1),
(2) Date: Sep. 10, 2021

(87) PCT Pub. No.: WO2020/185789
PCT Pub. Date: Sep. 17, 2020

(65) Prior Publication Data
US 2022/0250242 A1 Aug. 11, 2022

Related U.S. Application Data

(60) Provisional application No. 62/817,370, filed on Mar. 12, 2019.

(51) Int. Cl.
*B25J 9/16* (2006.01)
*A61B 34/30* (2016.01)
(Continued)

(52) U.S. Cl.
CPC ............. *B25J 9/1664* (2013.01); *A61B 34/37* (2016.02); *B25J 9/1633* (2013.01);
(Continued)

(58) Field of Classification Search
CPC ........ B25J 9/1664; B25J 9/1633; B25J 15/04; B25J 9/1689; A61B 34/37;
(Continued)

(56) References Cited

U.S. PATENT DOCUMENTS 5,431,645 A * 7/1995 Smith ................... A61B 10/06
606/1
6,645,196 B1 * 11/2003 Nixon ................... A61B 34/37
606/1

(Continued)

FOREIGN PATENT DOCUMENTS

CN 101421080 A 4/2009
CN 101528151 A 9/2009
(Continued)

OTHER PUBLICATIONS

International Search Report issued in corresponding international application No. PCT/US2020/021908 mailed Jul. 7, 2020 (4 pages).

(Continued)

*Primary Examiner* — Abby Y Lin
*Assistant Examiner* — Dylan M Katz
(74) *Attorney, Agent, or Firm* — Osha Bergman Watanabe & Burton LLP

(57) ABSTRACT

A computer-assisted medical system includes a manipulator arm and a controller. The controller includes a computer processor and is configured to determine a kinematic configuration, the kinematic configuration being prior to an installation of a replacement tool on the manipulator arm. The kinematic configuration is of the manipulator arm and a previous tool attached to the manipulator arm and with an end effector of the previous tool located at an insertion location. The controller is further configured to determine a reference geometry of the previous tool in the kinematic configuration, determine an insertion trajectory for the (Continued)

replacement tool based on the reference geometry, and facilitate an insertion of the replacement tool toward a target location of the insertion trajectory by controlling the replacement tool to move in accordance with the insertion trajectory.

34 Claims, 13 Drawing Sheets

(51) Int. Cl.
    *A61B 34/37*     (2016.01)
    *G05B 19/4155*     (2006.01)
    *B25J 15/04*     (2006.01)

(52) U.S. Cl.
    CPC .... *G05B 19/4155* (2013.01); *A61B 2034/301* (2016.02); *B25J 15/04* (2013.01); *G05B 2219/40269* (2013.01)

(58) Field of Classification Search
    CPC .... A61B 2034/301; A61B 2017/00477; A61B 2034/101; A61B 34/10; A61B 2034/107; A61B 2034/2059; A61B 2034/302; A61B 2090/371; A61B 2090/064; G05B 19/4155; G05B 2219/40269; G05B 2219/40117; G05B 2219/40191; G05B 2219/39468; G05B 2219/40375; G05B 2219/45117; G05B 2219/49146
See application file for complete search history.

(56) References Cited

U.S. PATENT DOCUMENTS

| | | | |
|---|---|---|---|
| 2011/0040305 A1* | 2/2011 | Gomez | A61B 34/74 606/130 |
| 2019/0059973 A1* | 2/2019 | Shelton, IV | A61B 18/1445 |
| 2022/0022982 A1* | 1/2022 | Hares | A61B 34/32 |

FOREIGN PATENT DOCUMENTS

| | | |
|---|---|---|
| WO | 0197694 A1 | 12/2001 |
| WO | WO-2011060042 A1 | 5/2011 |
| WO | WO-2013181516 A1 | 12/2013 |
| WO | WO-2014146090 A1 | 9/2014 |
| WO | 2015142796 A1 | 9/2015 |
| WO | WO-2017160458 A1 | 9/2017 |

OTHER PUBLICATIONS

Written Opinion of the International Searching Authority issued in corresponding international application No. PCT/ US2020/021908 mailed Jul. 7, 2020 (12 pages).

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

Same Length End Effector

| + | Previous Tool Tip |
| × | Replacement Tool Tip |
| - - - - | Previous Tool |
| ——— | Replacement Tool |

Short to Long End Effector

Same Length End Effector,
Limited Range of Motion at Wrist

Long to Short End Effector

Pivot Tool Shaft

GUIDED TOOL CHANGE

CROSS-REFERENCE TO RELATED APPLICATIONS

This patent application is a U.S. national phase application of International Application No. PCT/US2020/021908, which filed on Mar. 10, 2020. International Application No. PCT/US2020/021908 claims the benefit of priority under 35 U.S.C. § 119(e) to U.S. Provisional Patent Application Ser. No. 62/817,370, filed on Mar. 12, 2019. All mentioned U.S. patent applications, U.S. provisional patent applications, and international applications are incorporated by reference herein in their entirety.

BACKGROUND

Field of Invention

The present invention generally provides improved robotic and/or medical (including surgical) devices, systems, and methods.

Overview

A system of robotic devices can be used to perform a task at a worksite. For example, robotic systems may include robotic manipulators to manipulate instruments for performing the task. A robotic manipulator may include two or more links coupled together by one or more joints. The joints may be active joints that are actively moved and controlled. The joints may also be passive joints that comply with movement of the active joints or with external manipulation. Such active and passive joints may be revolute or prismatic joints. The configuration of the robotic manipulator may then be determined by the positions and orientations of the joints of the robotic manipulator, and by the structure of the robotic manipulator such as the design of the links of the robotic manipulator.

Example robotic systems include industrial and recreational robotic systems. Example, robotic systems also include medical robotic systems used in procedures for diagnosis, non-surgical treatment, surgical treatment, etc. As a specific example, robotic systems include minimally invasive, robotic telesurgical systems in which a surgeon may operate on a patient from bedside or a remote location. Telesurgery refers generally to surgery performed using surgical systems where the surgeon uses some form of remote control, e.g., a servomechanism, to manipulate surgical instrument movements rather than directly holding and moving the instruments by hand. A robotic medical system usable for telesurgery or other telemedical procedures may include a remotely controllable robotic manipulator. Operators may remotely control motion of the remotely controllable robotic manipulator. Operators may also manually move pieces of the robotic medical system into positions or orientations within its environment.

Robotic systems may be equipped with interchangeable tools. It may be desirable to efficiently exchange these tools in a simple manner while performing a robotic procedure.

Consider, for example, a scenario in which a robotic system is used to perform a surgery. A typical surgery employs a number of different surgical tools or instruments. When a different tool is desired during the surgical procedure, the surgical tool is typically withdrawn from the surgical site so that it may be removed from its associated manipulator arm and replaced with a tool having the desired end effector. The desired surgical tool is then inserted into the surgical site. A surgical tool may also be withdrawn from a surgical site for reasons other than to replace the end effector. For example, the loading of a clip in a clip applier used in affixing tissue typically occurs outside of the patient's body. Each time a new clip is desired, the clip applier is removed from the surgical site to load the clip and then reintroduced into the patient's body to apply the clip.

Continuing with the example describing a robotically performed surgery, a tool exchange for a robotic system takes time. Moreover, it may be difficult to bring the new tool into the field of view manually after a tool change operation. It is also possible for the operator to misjudge the depth of insertion and place the tool too deep into the surgical site, which may cause unintended contact between the tool and the patient's anatomy. To avoid such contact, the operator is likely to move the new tool very slowly into the surgical site. These factors contribute to make a tool change operation a time-consuming process.

For these and other reasons, it would be advantageous to provide improved devices, systems, and methods for robotic applications, including industrial, recreational, medical, and other robotic applications.

SUMMARY

In general, in one aspect, one or more embodiments relate to a computer-assisted medical system comprising: a manipulator arm; and a controller comprising a computer processor and configured to determine a kinematic configuration, the kinematic configuration being prior to an installation of a replacement tool on the manipulator arm, and the kinematic configuration being of the manipulator arm and a previous tool attached to the manipulator arm and with an end effector of the previous tool located at an insertion location. The controller is further configured to: determine a reference geometry of the previous tool in the kinematic configuration, determine an insertion trajectory for the replacement tool based on the reference geometry, and facilitate an insertion of the replacement tool toward a target location of the insertion trajectory by controlling the replacement tool to move in accordance with the insertion trajectory.

In general, in one aspect, one or more embodiments relate to a computer-assisted medical system, comprising: a manipulator arm; and a controller comprising a computer processor and configured to: determine a kinematic configuration, the kinematic configuration being prior to an installation of a replacement tool on the manipulator arm, and the kinematic configuration being of the manipulator arm and a previous tool attached to the manipulator arm and with an end effector of the previous tool located at an insertion location. The controller is further configured to determine a reference geometry of the previous tool in the kinematic configuration, detect an installation of the replacement tool on the manipulator arm, the replacement tool and the manipulator arm forming a physical manipulator assembly, determine a constraint trajectory for a virtual manipulator assembly based on the reference geometry, wherein the virtual manipulator assembly kinematically corresponds to the physical manipulator assembly. The controller is in addition configured to facilitate an insertion of the replacement tool toward a target location based on the insertion location by: determining a current kinematic configuration of the virtual manipulator assembly, the current kinematic configuration tracking the physical manipulator assembly and on the constraint trajectory, and controlling the physical manipulator assembly using the current kinematic configuration of the virtual manipulator assembly.

In general, in one aspect, one or more embodiments relate to a method for operating a medical system, comprising: determining a kinematic configuration, the kinematic configuration being of a manipulator arm and a previous tool attached to the manipulator arm and with an end effector of the previous tool inserted at an insertion location. The method further comprises determining a reference geometry of the previous tool in the kinematic configuration; detecting a removal of the previous tool from the manipulator arm; detecting an installation of a replacement tool on the manipulator arm; determining an insertion trajectory for the replacement tool based on the reference geometry; and facilitating an insertion of the replacement tool toward a target location of the insertion trajectory by controlling the replacement tool to move in accordance with the insertion trajectory.

In general, in one aspect, one or more embodiments relate to a method for operating a medical system, comprising: determining a kinematic configuration, the kinematic configuration being of a manipulator arm and a previous tool attached to the manipulator arm and with an end effector of the previous tool located at an insertion location. The method further comprises determining a reference geometry of the previous tool in the kinematic configuration; detecting a removal of the previous tool from the manipulator arm; detecting an installation of a replacement tool on the manipulator arm, the replacement tool and the manipulator arm forming a physical manipulator assembly; determining a constraint trajectory for a virtual manipulator assembly based on the reference geometry, wherein the virtual manipulator assembly kinematically corresponds to the physical manipulator assembly. In addition, the method comprises facilitating an insertion of the replacement tool toward a target location based on the insertion location by: determining a current kinematic configuration of the virtual manipulator assembly, the current kinematic configuration tracking the physical manipulator assembly and on the constraint trajectory, and controlling the physical manipulator assembly using the current kinematic configuration of the virtual manipulator assembly.

Other aspects of the invention will be apparent from the following description and the appended claims.

DETAILED DESCRIPTION

Figure 1A:
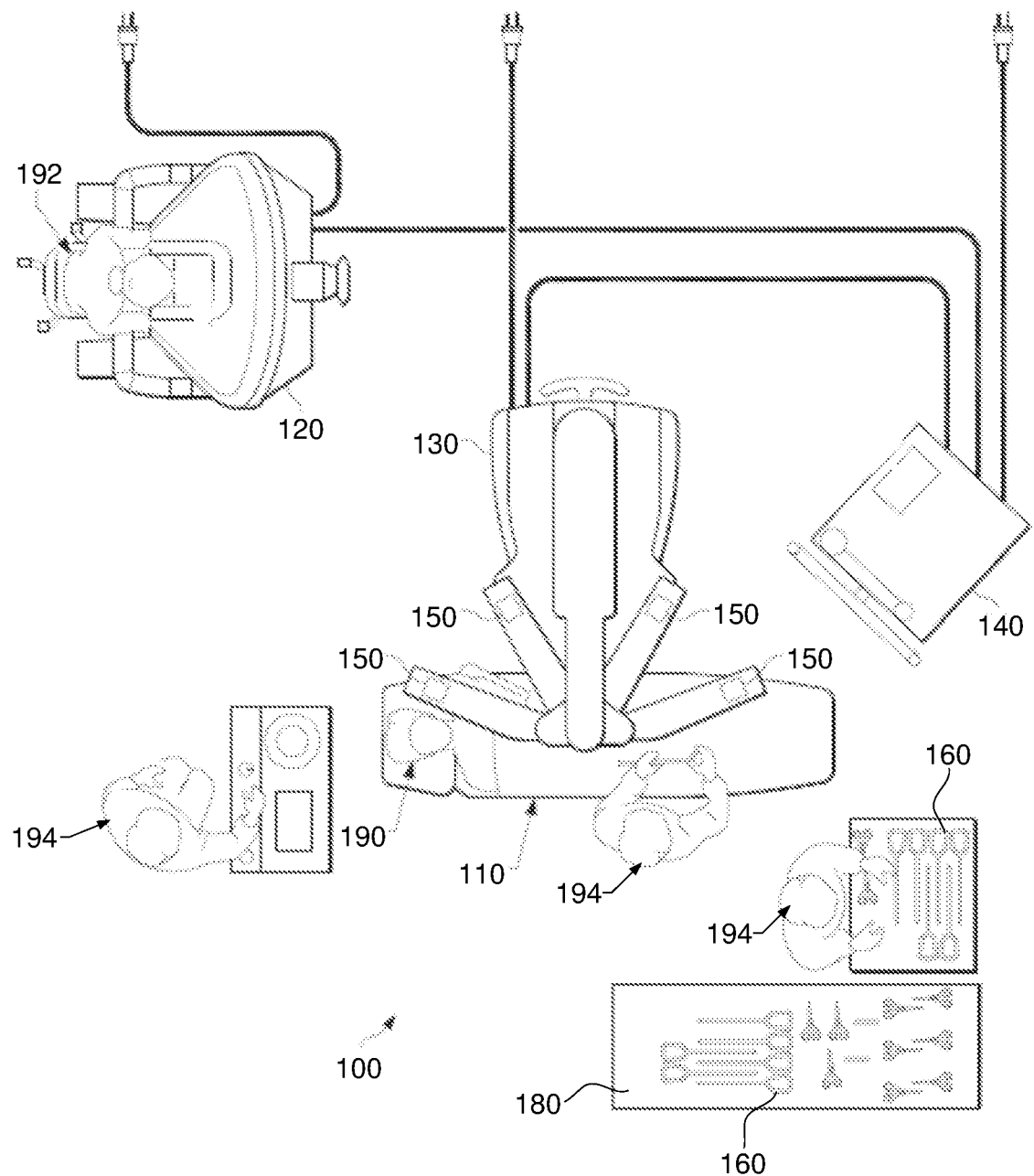
FIG. 1A shows an overhead view of a robotic procedure scenario in accordance with one or more embodiments.

Specific embodiments of the disclosure will now be described in detail with reference to the accompanying figures. Like elements in the various figures are denoted by like reference numerals for consistency.

In the following detailed description of embodiments of the disclosure, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as by the use of the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

Although some of the examples described herein refer to surgical procedures or tools, or medical procedures and medical tools, the techniques disclosed apply to medical and non-medical procedures, and to medical and non-medical tools. For example, the tools, systems, and methods described herein may be used for non-medical purposes including industrial uses, general robotic uses, and sensing or manipulating non-tissue work pieces. Other example applications involve cosmetic improvements, imaging of human or animal anatomy, gathering data from human or animal anatomy, setting up or taking down the system, and training medical or non-medical personnel. Additional example applications include use for procedures on tissue removed from human or animal anatomies (without return to a human or animal anatomy), and performing procedures on human or animal cadavers. Further, these techniques can also be used for medical treatment or diagnosis procedures that do, or do not, include surgical aspects.

In general, embodiments of the disclosure may support the replacement of an instrument or tool during a robotic procedure (e.g. a medical procedure such as a robotic imaging or surgical procedure) by facilitating the insertion of a replacement tool, after the previously used tool has been removed from the worksite (e.g. a medical procedure site such as a surgical site). In one or more embodiments, the replacement tool, when entering the worksite, follows an insertion trajectory defined based on the space previously occupied by the previously used tool and the kinematic configuration/range of motion of the replacement tool. A tip or end effector of the replacement tool may be guided toward a target location of the worksite. One or more degrees of freedom of the replacement tool, of the manipulator arm to which the replacement tool is attached, or of the replacement tool and the manipulator arm may be actively controlled during the insertion. In the case of a medical robotic system, embodiments of the disclosure thus provide the ability to have a replacement tool, when reentering the medical procedure site, generally follow the volume previously occupied by the previously used tool, in an effort to improve the workflow for inserting replacement tools.

In one or more embodiments, the replacement tool, while approaching the target location, adopts a kinematic configuration similar to the kinematic configuration of the previously used tool prior to removal, thereby facilitating the transition from the previously used tool to the replacement tool, for the operator.

In one or more embodiments, the replacement tool is inserted into the worksite, driven by an assistant manually exerting a driving force. To ensure that the replacement tool remains on the insertion trajectory, the replacement tool and/or the manipulator arm may provide force feedback to the assistant. A deviation from the insertion trajectory may result in an opposing force being provided to the assistant, thereby intuitively indicating the deviation to the assistant, and redirecting the replacement tool toward the insertion trajectory.

Embodiments of the disclosure may further provide additional features. For example, a capability of visually monitoring the end effector of the replacement tool as the end effector is being inserted, force control schemes that prevent a further insertion of the replacement tool when a resistance is encountered, and other features as discussed below, may be provided. Embodiments of the disclosure may thus enable a straightforward and efficient replacement of tools during robotic procedures. In the example of robotic surgeries, embodiments of the disclosure may reduce the likeliness of unintended interaction with tissue. Additionally, embodiments of the disclosure may enable the replacement tool to achieve a kinematic configuration similar to the previously used tool, thereby seamlessly and more accurately facilitating the transition from the previously used tool to the replacement tool for the operator. Additional features are discussed in the following description.

Referring now to the drawings, in which like reference numerals represent like parts throughout the several views, FIG. 1A shows an overhead view of a computer-assisted medical system (100) (hereinafter system (100)) in a robotic procedure scenario. While in FIG. 1A, a minimally invasive robotic surgical system is shown as the computer-assisted medical system (100), the following description is applicable to other scenarios and systems, e.g., non-surgical scenarios or systems, non-medical scenarios or systems. In the example, a diagnostic or surgical procedure is performed on a patient (190) who is lying down on an operating table (110). The system may include a user control system (120) for use by an operator (192) (e.g. a clinician such as a surgeon) during the procedure. One or more assistants (194) may also participate in the procedure. The system (100) may further include a robotic manipulating system (130) (e.g., a patient-side robotic device) and an auxiliary system (140). The robotic manipulating system (130) may include at least one manipulator arm (150), each of which may support a removably coupled tool (160) (also called instrument (160)). In the illustrated procedure, the tool (160) may enter the body of the patient (190) through a natural orifice such as the throat or anus, or through an incision, while the operator (192) views the worksite (e.g. a surgical site in the surgical scenario) through the user control system (120). An image of the worksite may be obtained by an imaging device (e.g. an endoscope an optical camera, or an ultrasonic probe), i.e., a tool (160) used for imaging the worksite, which may be manipulated by the robotic manipulating system (130) so as to position and orient the imaging device. The auxiliary system (140) may be used to process the images of the worksite for display to the operator (192) through the user control system (120) or other display systems located locally or remotely from the procedure. The number of tools (160) used at one time generally depends on the task and space constraints, among other factors. If it is appropriate to change, clean, inspect, or reload one or more of the tools (160) being used during a procedure, an assistant (194) may remove the tool (160) from the manipulator arm (150), and replace it with the same tool (160) or another tool (160), e.g., from a tray (180) or another type of tool storage.

Figure 1B:
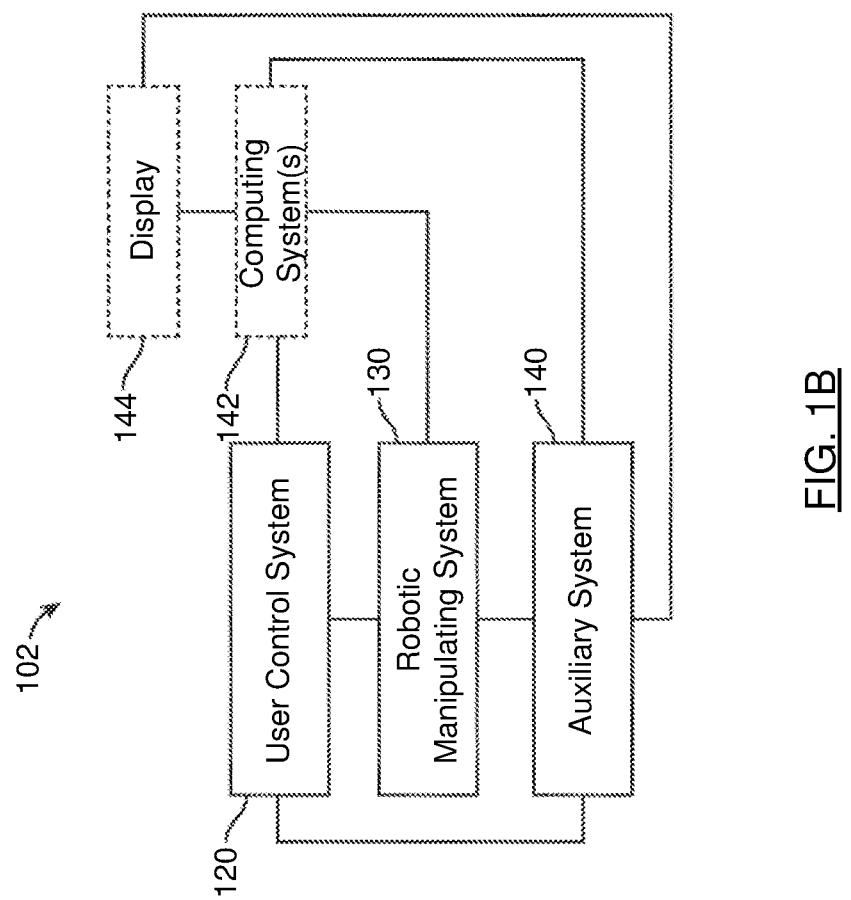
FIG. 1B diagrammatically shows various components of the robotic procedure scenario of FIG. 1A, in accordance with one or more embodiments.

FIG. 1B diagrammatically shows a system (100). The system (100) may include one or more computing systems (142). A computing system may be used to process input provided by the user control system (120) from an operator. A computing system may further be used to provide an output, e.g., a video image to the display (144). One or more computing systems (142) may further be used to control the robotic manipulating system (130).

A computing system (142) may include one or more computer processors, non-persistent storage (e.g., volatile memory, such as random access memory (RAM), cache memory), persistent storage (e.g., a hard disk, an optical drive such as a compact disk (CD) drive or digital versatile disk (DVD) drive, a flash memory, etc.), a communication interface (e.g., Bluetooth interface, infrared interface, network interface, optical interface, etc.), and numerous other elements and functionalities.

A computer processor of a computing system (142) may be an integrated circuit for processing instructions. For example, the computer processor may be one or more cores or micro-cores of a processor. The computing system (142) may also include one or more input devices, such as a touchscreen, keyboard, mouse, microphone, touchpad, electronic pen, or any other type of input device.

A communication interface of a computing system (142) may include an integrated circuit for connecting the computing system (142) to a network (not shown) (e.g., a local area network (LAN), a wide area network (WAN) such as the Internet, mobile network, or any other type of network) and/or to another device, such as another computing system (142).

Further, the computing system (142) may include one or more output devices (1308), such as a display device (e.g., a liquid crystal display (LCD), a plasma display, touchscreen, organic LED display (OLED), projector, or other display device), a printer, a speaker, external storage, or any other output device. One or more of the output devices may be the same or different from the input device(s). Many different types of computing systems exist, and the aforementioned input and output device(s) may take other forms.

Software instructions in the form of computer readable program code to perform embodiments of the disclosure may be stored, in whole or in part, temporarily or permanently, on a non-transitory computer readable medium such as a CD, DVD, storage device, a diskette, a tape, flash memory, physical memory, or any other computer readable storage medium. Specifically, the software instructions may correspond to computer readable program code that, when executed by a processor(s), is configured to perform one or more embodiments of the invention.

A computing system (142) may be connected to or be a part of a network. The network may include multiple nodes. Each node may correspond to a computing system, or a group of nodes. By way of an example, embodiments of the disclosure may be implemented on a node of a distributed system that is connected to other nodes. By way of another example, embodiments of the invention may be implemented on a distributed computing system having multiple nodes, where each portion of the disclosure may be located on a different node within the distributed computing system. Further, one or more elements of the aforementioned computing system may be located at a remote location and connected to the other elements over a network.

The robotic manipulating system (130) may use a tool (160) comprising an imaging device, e.g., an endoscope or an ultrasonic probe, to capture images of the worksite and output the captured images to an auxiliary system (140). The auxiliary system (140) may process the captured images in a variety of ways prior to any subsequent display. For example, the auxiliary system (140) may overlay the captured images with a virtual control interface prior to displaying the combined images to the operator via the user control system (120). The robotic manipulating system (130) may output the captured images for processing outside the auxiliary system (140). One or more separate displays (144) may also be coupled with a computing system (142) and/or the auxiliary system (140) for local and/or remote display of images, such as images of the procedure site, or other related images.

Figure 2:
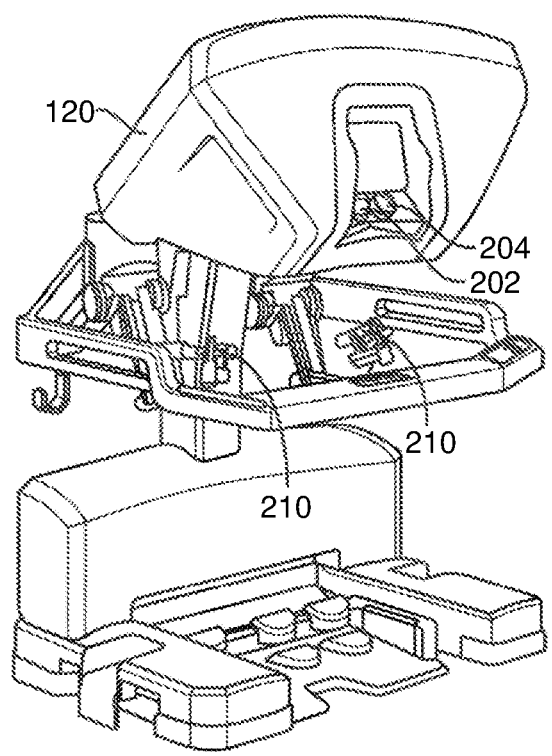
FIG. 2 shows a perspective view illustrating a master operator console or workstation for inputting procedure commands in the robotic assembly of FIG. 1A, in accordance with one or more embodiments.

FIG. 2 shows a perspective view of the user control system (120). The user control system (120) includes a left eye display (202) and a right eye display (204) for presenting the operator (192) (shown in FIG. 1A) with a coordinated stereo view of the worksite that enables depth perception. The user control system (120) further includes one or more input control devices (210), which in turn causes the robotic manipulating system (130) (shown in FIG. 1A) to manipulate one or more tools. The input control devices (210) may provide the same degrees of freedom as their associated tools (160) (shown in FIG. 1A) so as to provide the operator with telepresence, or the perception that the input control devices (210) are integral with the tools (160) (shown in FIG. 1A) so that the operator has a strong sense of directly controlling the tools (160). To this end, position, force, and/or tactile feedback sensors (not shown) may be employed to transmit position, force, and/or tactile sensations from the tools (160) back to the operator's hands through the input control devices (210).

Figure 3:
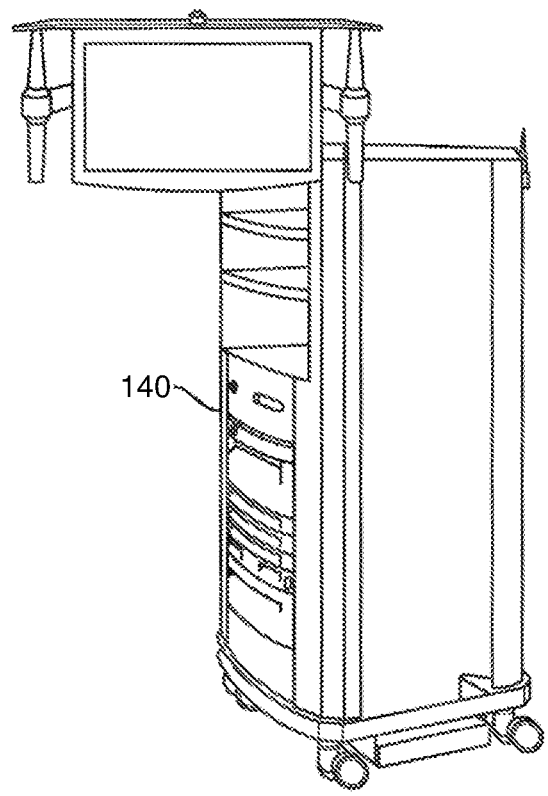
FIG. 3 shows a perspective view of the electronics cart of FIG. 1A, in accordance with one or more embodiments.

FIG. 3 shows a perspective view of the auxiliary system (140). The auxiliary system (140) may be coupled with the imaging device-type tool (160) (shown in FIG. 1A) and may include a processor (not shown) to process captured images for subsequent display, such as to an operator on the operator's console or on another suitable display located locally and/or remotely. For example, where a stereoscopic endoscope is used, the auxiliary system (140) may process the captured images so as to present the operator with coordinated stereo images of the worksite. Such coordination may include alignment between the opposing images and may include adjusting the stereo working distance of the stereoscopic endoscope. As another example, image processing may include the use of previously determined camera calibration parameters so as to compensate for imaging errors of the image capture device, such as optical aberrations.

Figure 4:
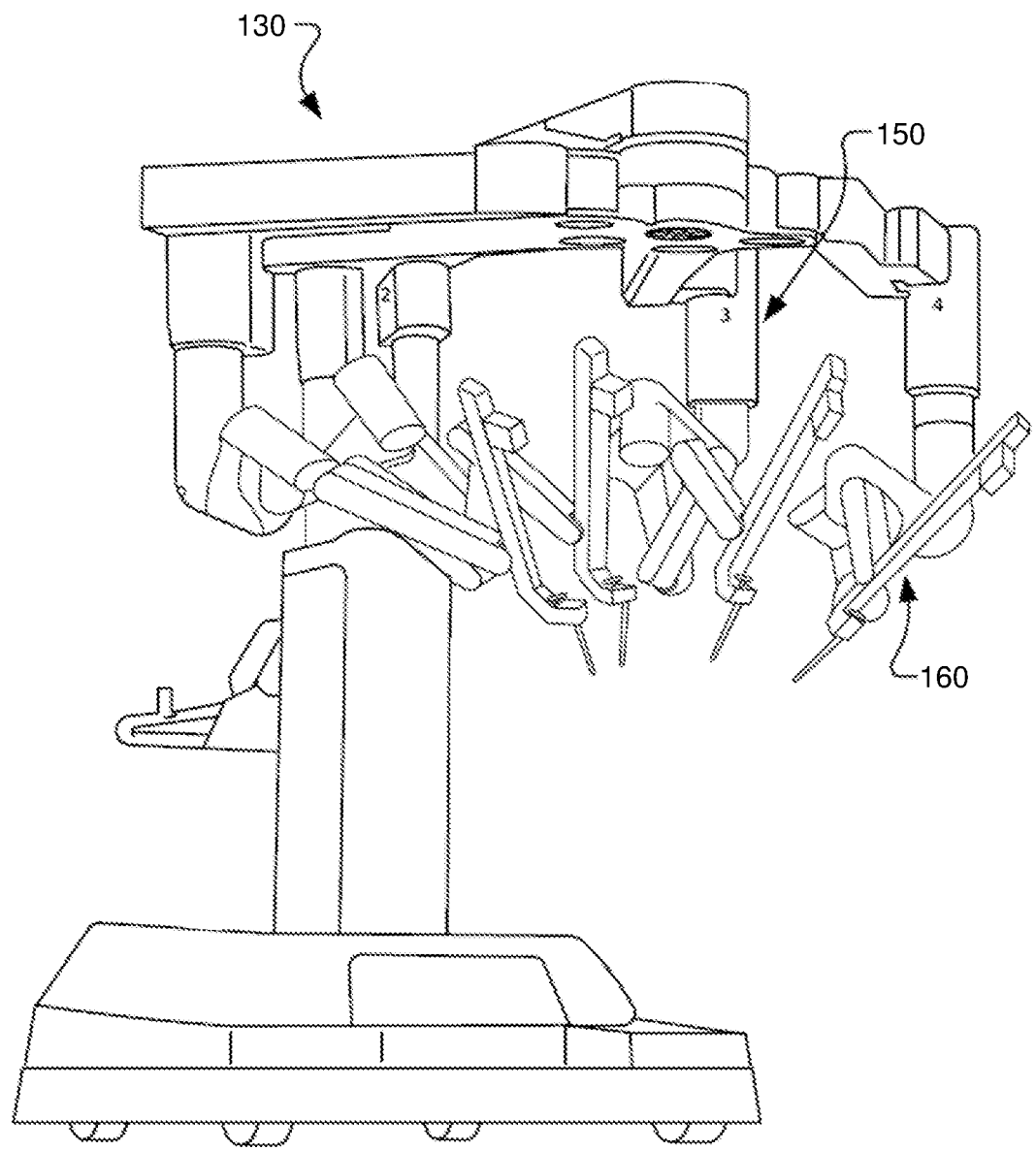
FIG. 4 shows a perspective view of a robotic assembly having four manipulator arms, in accordance with one or more embodiments.

FIG. 4 shows a robotic manipulating system (130) having a plurality of manipulator arms (150), each supporting an instrument or tool (160) at a distal end of the manipulator arm. The robotic manipulating system (130) as shown includes four manipulator arms (150), which may be used to support either a tool for manipulation (160) or tool for imaging (160), such as a stereoscopic endoscope used for the capture of images of the site of the procedure. A more detailed description of a manipulator arm (150) is provided below with reference to FIG. 5, and a more detailed description of a tool (160) is provided below with reference to FIGS. 6A, 6B, 6C, 6D, and 6E. In minimally invasive scenarios, the tools (160) may be positioned and manipulated through incisions in the patient so that a kinematic remote center is maintained at the incision so as to minimize the size of the incision or forces applied to tissue surrounding the incision. Images of the worksite may include images of the distal ends of the instruments or tools (160) when the tools (160) are positioned within the field-of-view of a tool operating as an imaging device.

A variety of tools (160) or instruments of different types and differing end effectors may be used. At least some of the tools (160) may be removed and replaced during a procedure. In surgical scenarios, the end effectors may include, but are not limited to, DeBakey forceps, microforceps, Potts scissors, clip appliers, scalpels and electrocautery probes. Some of these end effectors may have a single end effector element, while other end effectors may include multiple end effector elements, such as first and second end effector elements which may pivot relative to each other so as to define a pair of end effector jaws.

In surgical scenarios, an elongate shaft of a tool (160) allows the end effectors and the distal end of the shaft to be inserted distally into a surgical worksite through a minimally invasive aperture, often through a body wall such as an abdominal wall. The surgical worksite may be insufflated. Movement of the end effectors within the patient is often effected, at least in part, by pivoting of the tool (160) about the location at which the shaft passes through the minimally invasive aperture. Accordingly, manipulator arms (150) may move the proximal housing of the instrument outside the patient so that the shaft extends through a minimally invasive aperture to provide a desired movement of end effector. Hence, manipulator arms (150) may undergo movement outside the patient.

Figure 5:
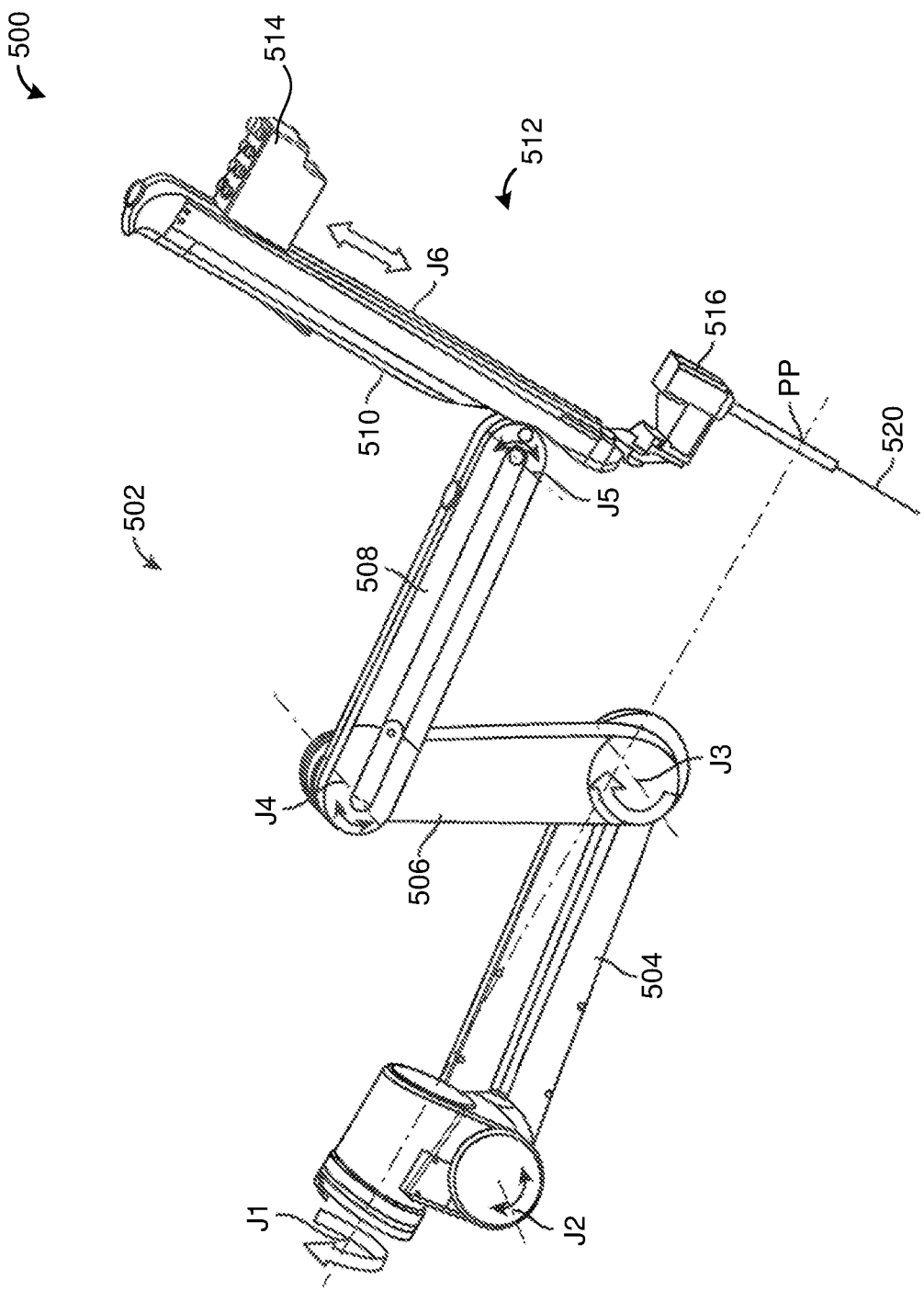
FIG. 5 shows an example of a manipulator arm assembly, in accordance with one or more embodiments.

An example of a manipulator assembly (500) in accordance with embodiments of the present disclosure is shown in FIG. 5. A manipulator assembly (500) may include a manipulator arm (502) and a tool (520) (also called instrument (520)) (in FIG. 5, only an axis of the tool, but not the tool itself, is shown). As described above, during operation, the manipulator arm (502) generally supports a distal instrument or tool (520) and effects movements of the tool (520). As a number of different tools (520) having differing end effectors may be sequentially mounted on a manipulator arm (502), or as a tool (520) needs to be removed and reinstalled during a procedure, a distal tool holder facilitates removal and replacement of the mounted instrument or tool. As may be understood with reference to FIG. 4, manipulator arms (502) are proximally mounted to a base of the robotic assembly. Alternatively, manipulator arms (502) may be mounted to separate bases that may be independently movable, e.g., by the manipulator arms (502) being mounted to single-manipulator-arm carts, being provided with mounting clamps that allow mounting of the manipulator arms (502) directly or indirectly to the operating table (shown in FIG. 1A) at various locations, etc. Typically, a manipulator arm (502) includes a plurality of manipulator arm segments and associated joints extending between the proximal base and the distal tool holder.

In embodiments such as shown for example in FIG. 5, a manipulator arm includes multiple joints (such as revolute joints J1, J2, J3, J4, and J5, and prismatic joint J6) and links or manipulator arm segments (504, 506, 508, and 510) The joints of the manipulator arm, in combination, may or may not have redundant degrees of freedom. A manipulator arm with one or more redundant degrees of freedom have a plurality of joints such that the plurality of joints may be driven into a range of differing configurations for a given position and orientation of a portion of the manipulator arm. For example, a manipulator arm with one or more redundant degrees of freedom may have a plurality of joints that may be driven into a range of differing configurations for a given position and orientation of a distal portion or end effector of the manipulator arm. For example, the manipulator arm (502) of FIG. 5 may be maneuvered into differing configurations while the distal member (512) supported within the tool holder (510) maintains a particular state and may include a given position or velocity of the end effector. The tool holder (510) may include a cannula (516) through which the tool shaft of the tool (520) extends, and the tool holder (510) may comprise a carriage ((514) shown as a box-shaped structure that translates on a spar) to which the tool attaches before extending through the cannula (516) toward the worksite.

Actuation of the degrees of freedom of the tool (520) is often provided by actuators of the manipulator. These actuators may be integrated in the carriage (514). A distal wrist of the tool may allow pivotal and/or linear motion of an end effector of the tool (520) about tool joint axes of one or more joints at the tool wrist. An angle between end effector jaw elements may be controlled independently of the end effector location and orientation. A detailed description of the tool (520) is provided below with reference to FIGS. 6A, 6B, 6C, 6D, and 6E.

Figure 6A:
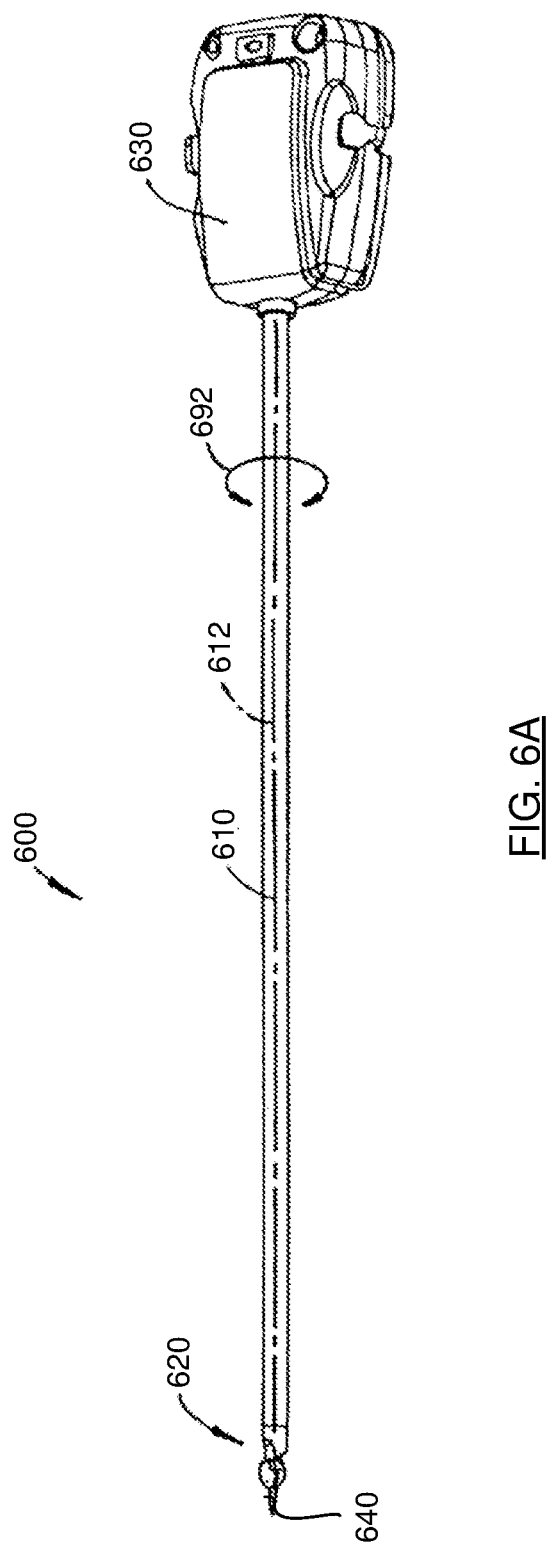
FIG. 6A shows a perspective view of a tool or instrument, in accordance with one or more embodiments.

FIG. 6A shows an example of a tool (600) (also called instrument (600)) as it may be used for surgery, in accordance with one or more embodiments. The tool (600) includes an elongate shaft (610) and a wrist (620) located at a working end of the shaft (610). A housing (630), arranged releasably to couple the tool (600) to manipulator arm (502), is located at an opposed end of the shaft (610). The shaft (610) may be rotatably coupled to the housing (630) to enable angular displacement of the shaft (610) relative to the housing (630) as indicated by arrows (692) thereby allowing a rotation of the end effector (640) coupled to the shaft via the wrist (620). Various embodiments of tool (600) have multi-degree-of-freedom wrists (e.g. pitch and yaw degrees of freedom), single-degree-of-freedom wrists (e.g. pitch or jaw), or no wrists.

In FIG. 5, when the tool (520) is coupled or mounted on the manipulator arm (502), the shaft (610) extends through the cannula (516). The tool (520) typically is releasably mounted on a tool holder (510) of the manipulator arm (502), which may be driven to translate along a linear guide formed by prismatic joint (J6). This may also be referred to as the "IO", and provide in/out movement along the insertion axis (612). The housing (630) may include spools that are rotatable to control cables to actuate linkages of the end effector (640), as described in U.S. Pat. No. 6,394,998, entitled "Surgical Tools for Use in Minimally Invasive Telesurgical Applications." A more detailed description of the end effector (640) is provided below, with reference to FIGS. 6B, 6C, 6D, and 6E. The tool holder (510) of the manipulator arm (502) may include disks for coupling with the spools to drive the spools upon connection of the tool (600) to the manipulator arm (502).

Turning to FIGS. 6B, 6C, 6D, and 6E, a wrist (620) and an end effector (640) of a tool (such as the tool (600) introduced in FIG. 6A), in accordance with one or more embodiments, are shown. Each tool shown in FIGS. 6B-6E comprises a wrist (620) disposed on a working end of its shaft (610). The wrist (620) may enable a pivoting of the end effector (640B, 640C, 640D, and 640E) relative to the shaft (610). The wrist (620) may have at least one degree of freedom.

Different types of tools (600) may have different end effectors with different geometries, degrees of freedom, and/or functions. For example, the end effector (640B) in FIG. 6B includes a single member forming a cautery hook; the end effector (640C) in FIG. 6C includes two members in a jaw-like arrangement forming a forceps; the end effector (640D) in FIG. 6D includes a single member forming a nozzle of an irrigator or suction device; and the end effector (640E) in FIG. 6E includes two members in a jaw-like arrangement forming a clip applier. The end effector (640C and 640E) may be in the form of any desired tool, e.g., having two members or fingers which pivot relative to each other, such as a clip applier for anchoring clips (as shown in FIG. 6E), scissors, two-fingered blunt dissection tools, forceps (as shown in FIG. 6C), pliers for use as needle drivers, or the like. Both members of the end effector (640C and 640E) may be individually angularly displaceable, thereby not only allowing an opening and closing of the end effector, but also enabling an angular displacement to change the orientation of the end effector (640C and 640E) as a whole, relative to the wrist (620).

Figure 6B:
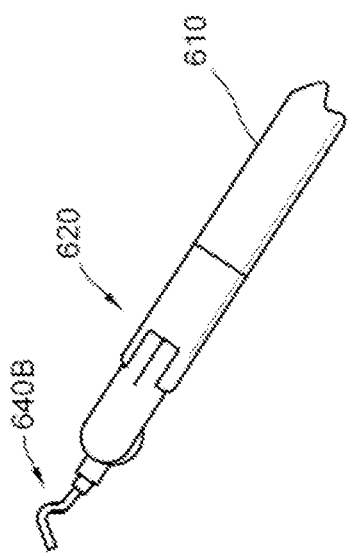
FIG. 6B, FIG. 6C, FIG. 6D, and FIG. 6E, show perspective views of wrists and end effectors of the tool or instrument shown in FIG. 6A, in accordance with one or more embodiments.
Figure 6C:
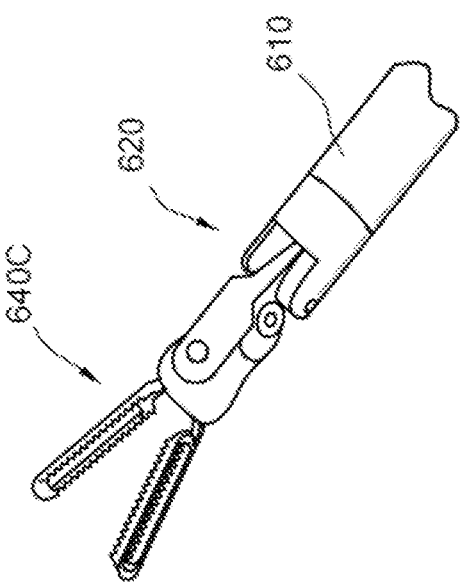
Figure 6D:
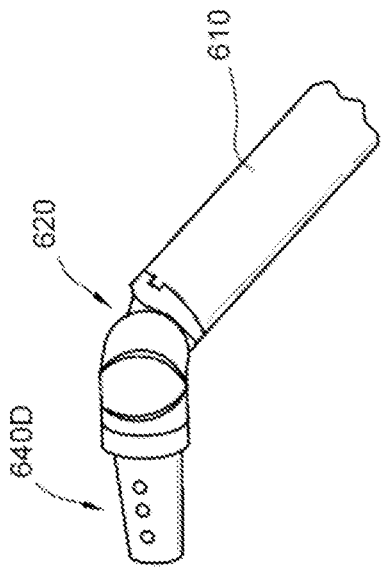
Figure 6E:
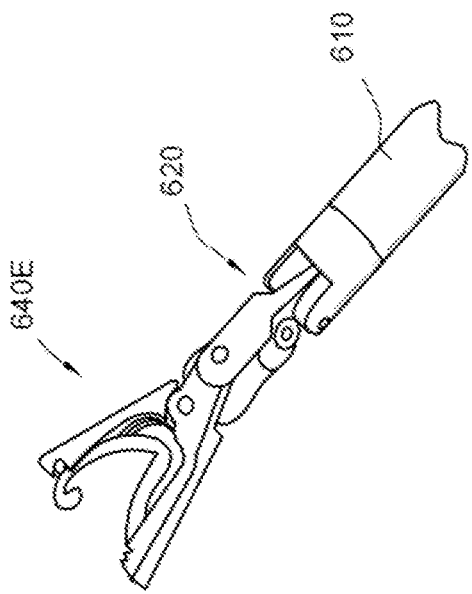

Moreover, the end effector (640B and 640D) may include a single working member, e.g., a scalpel, cautery electrode (as shown in FIG. 6B), irrigation device (as shown in FIG. 6D) or the like. Other end effector configurations may exist, without departing from the disclosure. An imaging device may also be considered to have an end effector (640) (i.e., one for obtaining images), and like other end effectors may be coupled to the shaft (610) of the tool with or without a wrist.

When a different tool (600) is desired during the procedure, the tool (600) is removed from its associated arm and replaced with another tool (600) having the desired end effector (640). A tool (600) may also be removed and reinserted, for example, to clean the tool, to inspect the tool, to reload the tool (e.g., by loading a clip applier with a clip, loading a stapler with a stapler cartridge), etc.

The degrees of freedom of the end effector (640) may be controlled by appropriately positioned actuators, e.g., electrical motors, which respond to inputs from the associated input control devices (e.g. input control devices (210) in FIG. 2) to drive the end effector (640) to a desired orientation as dictated by movement of the input control devices (210) or any other control signal. Furthermore, appropriately positioned sensors, e.g., encoders, potentiometers, etc., may be provided to enable measurement of the joint positions. The actuators and sensors may be disposed in the carriage (514) of the tool holder (510), shown in FIG. 5.

While FIG. 1A, FIG. 1B, FIG. 2, FIG. 3, FIG. 4, FIG. 5, FIG. 6A, FIG. 6B, FIG. 6C, FIG. 6D, and FIG. 6E show various configurations of components, other configurations may be used without departing from the scope of the invention. For example, various components may be combined to create a single component. As another example, the functionality performed by a single component may be performed by two or more components. Further, while the components are described in context of surgical scenarios, embodiments of the disclosure may be equally applicable to other domains that involve robotic manipulation.

Figure 7:
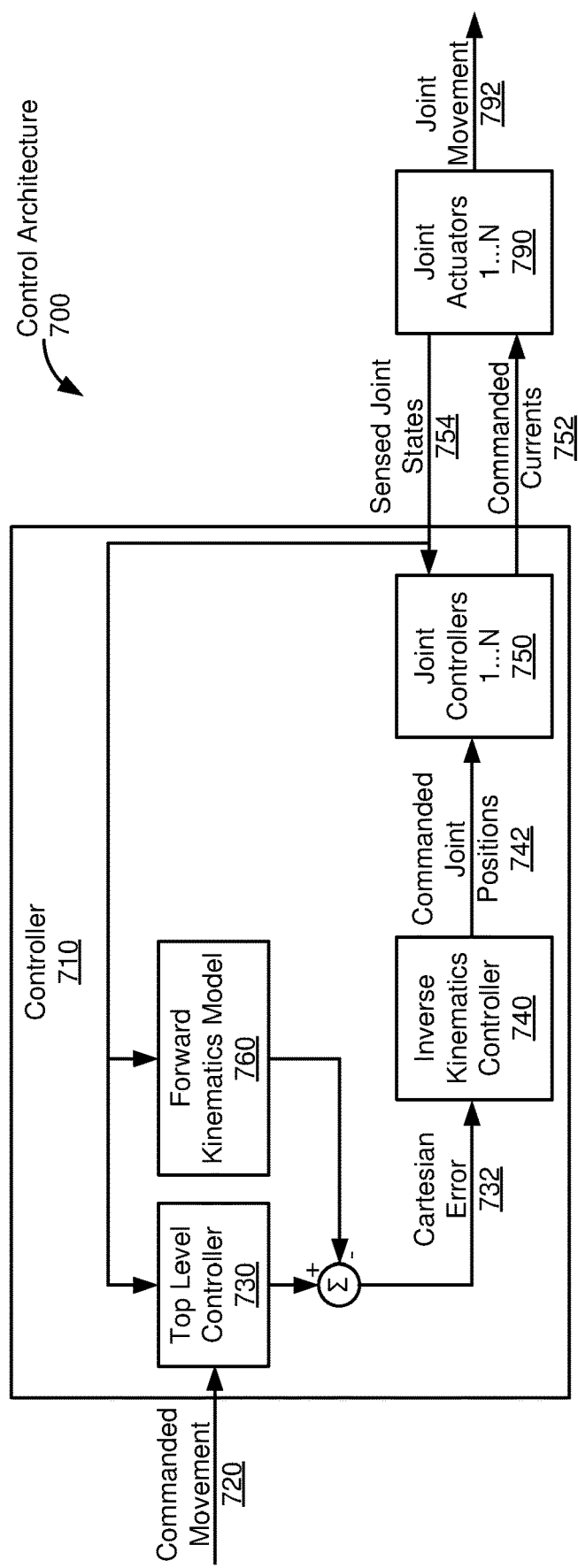
FIG. 7 shows a control architecture for controlling a robotic assembly, in accordance with one or more embodiments.

Turning to FIG. 7, a control architecture for controlling a manipulator assembly including a manipulator arm and an instrument or tool mounted thereon, in accordance with one or more embodiments, is shown. One control architecture is illustrated as an example. Those skilled in the art will appreciate that other control architectures may be used without departing from the disclosure. Further, in the illustrated control architecture, particular signals (e.g. positions) are exchanged between blocks of the control architecture. Other signals (e.g., velocities, accelerations, forces, etc.) may be used, without departing from the disclosure. Also, the control architecture may implement different modes (not shown). For example, during a robotic task being performed under the control of input control devices (210) operated by a user as illustrated in FIG. 2, various joints of the robotic manipulator assembly may be position-controlled. However, in another control mode, e.g., during a tool exchange, one or more of the joints may be "floating", allowing an assistant to readily externally articulate these one or more joints, such as by back-driving these one or more joints. A floating joint may be back-driven by an externally applied force without a control algorithm or a braking force counteracting sufficient externally applied force. For example, a user may apply a force meeting one or more criteria (e.g., for magnitude, direction, duration, frequency) to a link distal to the floating joint, causing the back-driving of the floating joint. A floating joint, in particular when floating in a degree of freedom affected by gravity (e.g. a "vertical" joint or in a "non-horizontal" direction), may further be gravity-compensated. In addition, a friction compensation may facilitate the back-driving. Additionally or alternatively, a floating joint may also be controlled to impose other characteristics such as a certain level of damping. Multiple control modes may be combined during operation of the manipulator assembly, e.g., some joints may be position controlled to resist or rebound from external articulation of those joints, while other joints may be floating and facilitate external articulation of those other joints. In addition, one or more joints of the manipulator assembly may be passive, i.e., not position or velocity controlled at all. Passive joints may be manually operated by an assistant. Passive joints may, nevertheless, include joint sensors such that the full kinematics of the manipulator assembly may be obtained. Further, in some embodiments, passive joints may contain actuators for supplying gravity compensation, friction compensation, or other utility not including actively driving the motion of the passive joint.

In one or more embodiments, the joint movements of the manipulator assembly are controlled by driving one or more joints by a controller using actuators (e.g. motors, solenoids, etc.) of the manipulator assembly, the joint movements being calculated by a processor of the controller. Mathematically, the controller may perform at least some of the calculations of the joint commands using vectors and/or matrices, some of which may have elements corresponding to positions, velocities, and/or forces/torques of the joints. The range of alternative joint configurations available to the processor may be conceptualized as a joint space. The joint space may, for example, have as many dimensions as the manipulator assembly has degrees of freedom, and a particular configuration of the manipulator assembly may represent a particular point in the joint space, with each coordinate corresponding to a joint state of an associated joint of the manipulator assembly.

As used herein, the term "state" of a joint or multiple joints refers to the control variables associated with the joint or the multiple joints, respectively. For example, the state of an angular joint may refer to the angle defined by that joint within its range of motion, and/or to the angular velocity of the joint. Similarly, the state of an axial or prismatic joint may refer to the joint's axial position, and/or to its axial velocity. While one or more of the controllers described herein include position controllers, they often also have velocity control aspects. Alternative embodiments may rely primarily or entirely on velocity controllers, force controllers, acceleration controllers, etc. without departing from the disclosure. Many aspects of control systems that may be used in such devices are more fully described in U.S. Pat. No. 6,699,177, the full disclosure of which is incorporated herein by reference. Hence, so long as the movements described are based on the associated calculations, the calculations of movements of the joints and movements of an end effector described herein may be performed using a position control algorithm, a velocity control algorithm, a combination of both, etc.

The control architecture (700) of FIG. 7 includes a controller (710) that drives joint actuators (790) of the manipulator assembly based on a commanded movement (720). Any number of joint actuators (790) may be driven.

The commanded movement (720) may be a commanded position and/or velocity of one or more features in the work-space, in Cartesian-coordinate space (referred to herein as Cartesian-space). The commanded movement (720) may be, for example, a movement command (e.g., in the form of a position and/or velocity) received from the user control system (120), or any other movement command of one or more features of the manipulator arm. A feature may be any feature physically on the manipulator assembly, or physically off the manipulator assembly, which may be used to define a control frame to be articulated using control inputs. Examples of features on the manipulator assembly include features of a tool (e.g., an end effector tip, a central point on the end effector, or a clevis of the end effector), a feature of the manipulator arm (e.g., an instrument holder configured to physically couple with a removable instrument). Another example of a feature of the manipulator assembly is a reference point in empty space which is exactly a certain distance and angle away from the end effector tip. Another example of a feature off the manipulator assembly is a target tissue whose position relative to a part of the manipulator assembly may be established.

The controller (710) may include a top level controller (730), an inverse kinematics controller (740), joint controllers (750), and a forward kinematics model (760). Each of these components is subsequently described.

The top level controller (730), in accordance with one or more embodiments, includes instructions in the form of computer readable program code to receive the commanded movement (720), and to convert the commanded movement (720) into positions in a Cartesian reference frame. The steps performed to convert the commanded movement (720) into Cartesian positions depend on the format in which the commanded movement (720) is provided. For example, if the commanded movement (720) specifies a desired end effector position, the top level controller (730) may perform trajectory planning using, for example, a position-time (PT) or position-velocity-time (PVT) interpolation. Alternatively, if the commanded movement (720) includes a velocity command, the top level controller (730) may operate as an integrator. Those skilled in the art will appreciate that the top level controller (730) may perform any operation necessary to obtain a position signal in a Cartesian reference frame. In one or more embodiments, the top level controller (730) generates the Cartesian positions from the commanded movement (720) under consideration of the sensed joint states (754). The sensed joint states (754) may enable the top level controller to determine an actual state (e.g., including current position and/or velocity, etc. of the joints to be controlled. The actual state may affect the control task and, therefore, may be considered by the top level controller. For example, for a particular configuration of the manipulator assembly, a commanded movement may be undesirable and may, thus not be executed or alternatively may be converted into an alternative commanded movement that may be executed in a desirable manner.

The inverse kinematics controller (740), in accordance with one or more embodiments, includes instructions in the form of computer readable program code to convert commanded Cartesian positions (732) into commanded joint positions (e.g., joint angles for rotary joints) (742). The operations by the inverse kinematics controller (740) may be performed in the velocity domain. In other words, the inverse kinematics controller (740) may seek to determine or solve for a joint velocity vector that may be used to drive the joints of the manipulator assembly in such a way that the end effector accurately follows the commanded Cartesian positions. The inverse kinematics controller (740) may integrate the computed joint velocities to obtain command joint positions (742).

The commanded Cartesian error (732) may be a combination of the Cartesian positions provided by the top level controller (730), as previously discussed, and Cartesian positions provided by a forward kinematics model (760), discussed below. More specifically, the Cartesian positions provided by the forward kinematics model (760) may represent an estimate of an actual or current position (e.g., of an end effector), in Cartesian space, of the manipulator assembly. This estimate may be subtracted, from the Cartesian positions representing the commanded movement, to obtain the difference to be compensated for, to be used as the control input to the inverse kinematics controller (740).

While generally there may not be a closed form relationship which maps a desired Cartesian space position to an equivalent joint-space position, a closed form relationship between the Cartesian space velocity and joint-space velocities typically exists. The kinematics Jacobian is the matrix of partial derivatives of Cartesian space position elements with respect to joint space position elements. In this way, the Jacobian captures the kinematic relationship between, for example, the end effector and the joints. In other words, the Jacobian captures the effect of joint motion on the end effector. The Jacobian (J) may be used to map joint-space velocities (dq/dt) to Cartesian space velocities (dx/dt), e.g., end effector velocities.

Thus, even when there is no closed-form mapping between input and output positions, mappings of the velocities may iteratively be used by the inverse kinematics controller (740) to implement a movement of the manipulator assembly based on a commanded trajectory. One such implementation is subsequently described in simplified terms. Assume that the commanded movement (720) includes Cartesian positions provided at time steps, Δt. At each time step (Δt), a Cartesian velocity (dx/dt) is calculated by the inverse kinematics controller (740) to perform the desired movement and to correct for built up deviation from the desired Cartesian position (obtained by the subtraction of the Cartesian position produced by the forward kinematics model (760)). This commanded Cartesian position (or Cartesian error (732), after subtraction of the output of the forward kinematics model) is then converted into a commanded joint position (q) (742) using the pseudo-inverse of the Jacobian (J #), in the velocity domain. The commanded joint position is used to re-calculate the Jacobian (J), which may be used for the calculations performed for the next time step. The described steps may be performed for any number of joints.

Some of the example manipulator assemblies described herein have more degrees of freedom than are needed to position and move an end effector within a worksite. For example, a surgical end effector that may be positioned with six degrees of freedom at an internal surgical site through a minimally invasive aperture may in some embodiments have a nine degrees of freedom task space (six end effector degrees of freedom—three for location, and three for orientation—plus three degrees of freedom to comply with the access site constraints), but may have ten or more degrees of freedom. Highly configurable manipulator arm assemblies having more degrees of freedom than are needed for a given end effector position may be described as having or providing sufficient degrees of freedom to allow a range of joint states for an end effector position in a workspace. For example, for a given end effector position, the manipulator assembly may occupy (and be driven between) any of a range of alternative manipulator arm configurations. Similarly, for a given end effector velocity vector, the manipulator assembly may have a range of differing joint movement speeds for the various joints of the manipulator assembly within the null-space of the Jacobian.

When directing movement of highly configurable manipulators with redundant degrees of freedom, the inverse Jacobian generally does not fully define a joint vector solution. For example, the mapping from a Cartesian command (x) to joint position (q) in a system that may occupy a range of joint states for a given end effector state is a mapping of one-to-many. In other words, because the mechanism is redundant, there are a mathematically infinite number of solutions, represented by a subspace in which the inverse lives. Additional constraints may be imposed to arrive at a unique solution. Those skilled in the art will appreciate that various methods may be used to perform inverse kinematics, including inverse kinematics for manipulators with redundant degrees of freedom.

Each of the joint controllers (750), in accordance with one or more embodiments, includes instructions in the form of computer readable program code to convert a received commanded joint position (742) into a commanded current (752) to drive one of the joint actuators (790) producing a joint movement (792). One joint controller (750) may be used per joint actuator (790). The joint movements (792) of all joint actuators through the kinematics of the manipulator assembly may produce a manipulator arm movement that reflects the commanded movement (720). In one embodiment of the disclosure, the joint controller controls a joint position or angle. Alternatively, the joint controller may control other variables such as joint velocity, joint torque or joint force (in case of a linear joint). A joint controller (750) may receive a feedback signal in the form of a sensed joint state (754) from the associated joint actuator (790) to enable closed-loop control. The sensed joint state (754) provided by the joint actuator (790) may include a joint position, a joint velocity, and/or a joint acceleration, etc., representing the joint movement (792). The sensed joint state may be derived from signals obtained from a sensor attached to the joint. Such a sensor may be, for example, an incremental encoder or a hall sensor of the joint actuator. A state observer or estimator (not shown) may be used. Each joint controller (750) may implement a proportional integral derivative (PID), proportional derivative (PD), full state feedback, sliding mode, or various other control schemes, without departing from the disclosure.

The forward kinematics model (760), in accordance with one or more embodiments, includes instructions in the form of computer readable program code to convert the sensed joint states (754) into Cartesian positions and/or velocities, as previously discussed.

The controller (710) may be implemented on one or more computing systems. These one or more computing systems may be based on digital signal processors (DSPs), central processing units (CPUs), etc. An example computing system is described with reference to FIG. 1B. Each of the computing systems may perform the described operations at a cycle time that depends on the nature of the operations. In one embodiment, the cycle times of the inverse kinematics controller (740) and the joint controllers (750) are identical. The communication between the computing systems implementing the top level controller (730), the inverse kinematics controller (740), and the joint controllers (750) may be performed using any type of electrical or optical communication networks, including Ethernet, fiber optics, various bus systems, and/or any other type of digital or analog signals.

Figure 9:
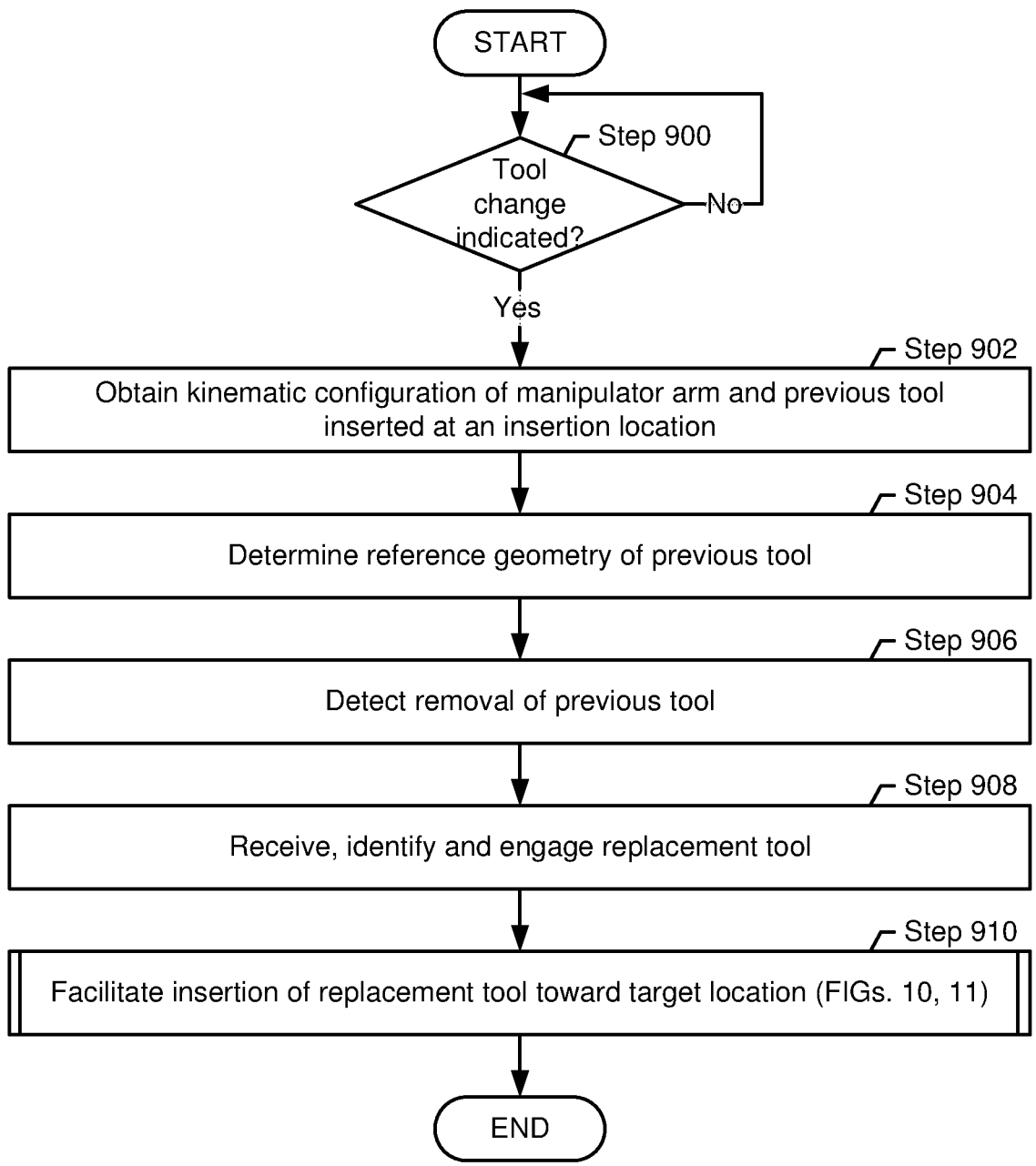
FIG. 9 shows a flowchart describing a method for a guided tool change, in accordance with one or more embodiments.
Figure 10:
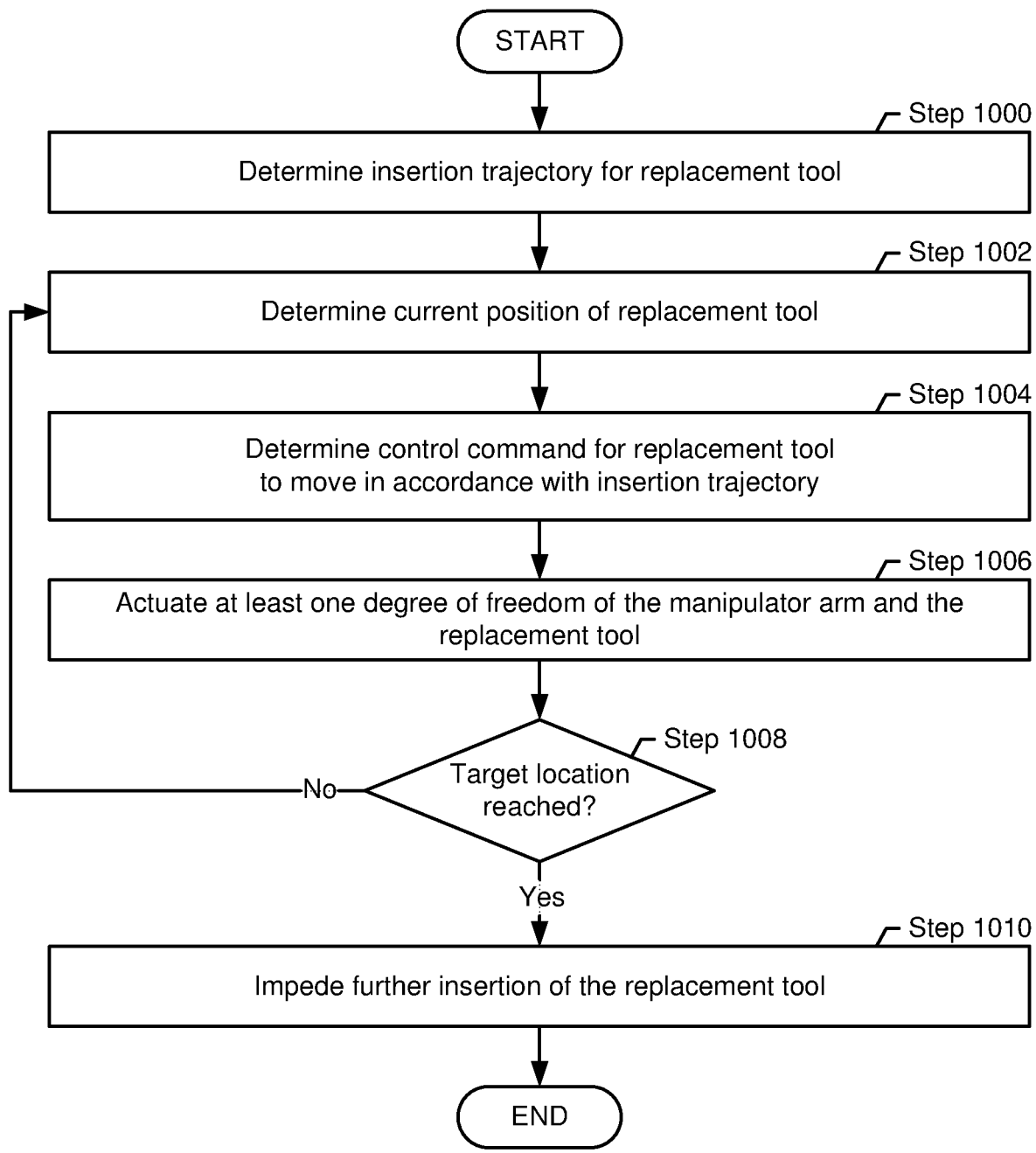
FIG. 10 shows a flowchart describing a method for controlling the kinematic configuration of a replacement tool during the insertion of the replacement tool, in accordance with one or more embodiments.
Figure 11:
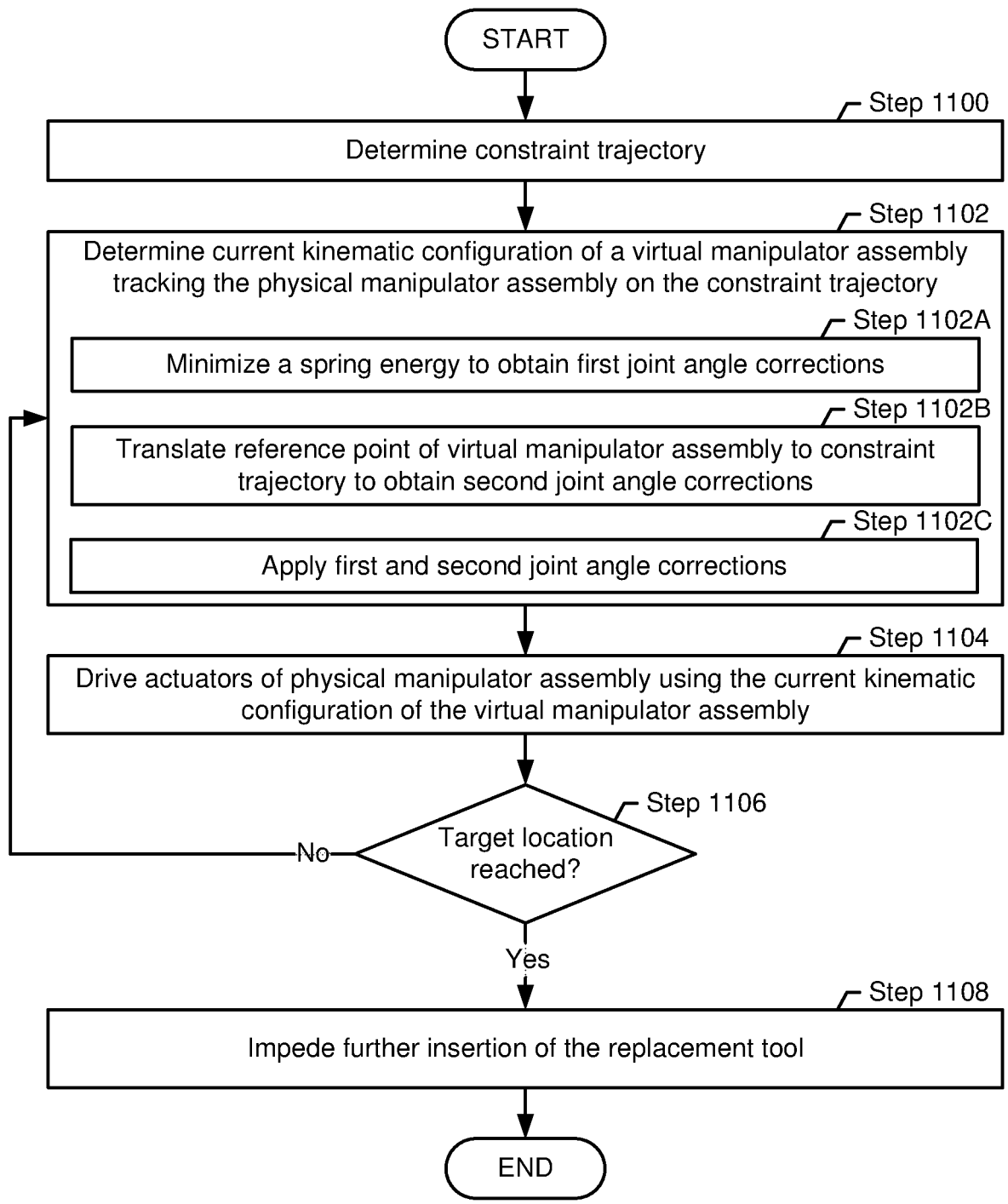
FIG. 11 shows a flowchart describing a method for a controlling the kinematic configuration of a replacement tool during the insertion of the replacement tool while providing force feedback to an assistant performing the insertion, in accordance with one or more embodiments.

In one or more embodiments, the controller (710) is further configured to perform at least one of the steps described in FIGS. 9, 10, and 11.

Figure 8A:
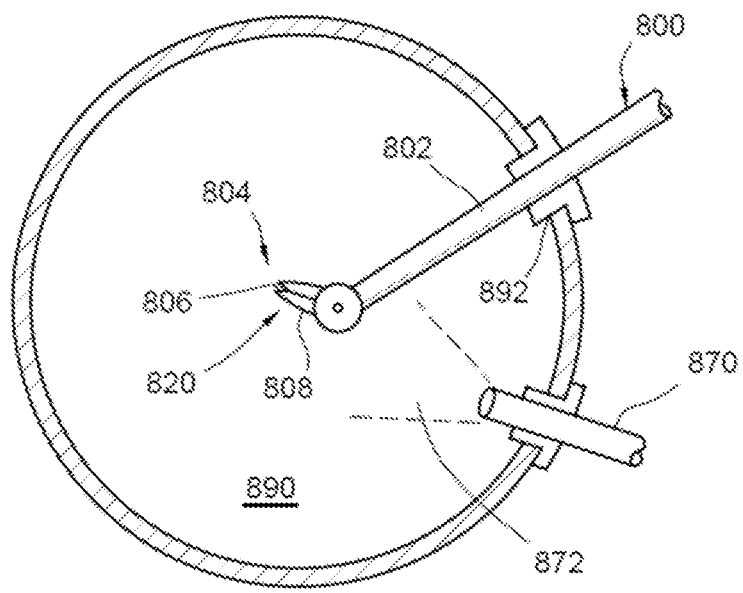
FIG. 8A schematically shows a tool at a worksite, in accordance with one or more embodiments.

Turning to FIG. 8A, a tool at a worksite, in accordance with one or more embodiments, is schematically shown.

FIG. 8A shows a tool (800) including a shaft (802) and an end effector (804) having a distal end tool tip (806). A wrist (808) pivotally connects the end effector (804) to the shaft (802). The tool (800) may be substantially similar to one of the tools introduced in FIGS. 6A 6B, 6C, 6D, and 6E, or be another type of tool. As shown in FIG. 8A, the tool (800) is inserted into a worksite (890) via an aperture (892). The tool is shown at an insertion location (820). The insertion location (820) may be defined, for example, as the location prior to removal of a part of the tool (800) (e.g. the tool tip (806), a central location of the end effector (804), a clevis for a jawed end effector (804), or some other part of the tool (800)). When the tool (800) is inserted in the worksite (890), the insertion location is a location in the worksite (890). In a surgical scenario, the worksite (890) may be a cavity of a patient's body. The shaft (802) and the end effector (804) are controlled from outside the worksite (890). A manipulator arm similar to the manipulator arm introduced in FIG. 5, having one or more actuators, may be used to control a mounted tool (800), such as by driving motion of the shaft (802) or any joints of the tool (800), including that of the end effector (804). FIG. 8A further shows a second tool (870) comprising an imaging device. The imaging device of the second tool (870) may capture a field of view (872), which may be provided to an operator and/or an assistant. The field of view (872) may cover the location of the end effector (804) of the tool (800) and may further cover an area surrounding the end effector (804). While two particular tools (800, 870) with specific geometries and degrees of freedom are shown, those skilled in the art will appreciate that tools may have any appropriate geometry, and may include any number of joints of any type (e.g. cylindrical joints, prismatic joints, etc.), be flexible or rigid, or have any number of degrees of freedom. The tools (800, 870) may also be any other type of instrument than shown in FIG. 8A. The tool (800), as shown in FIG. 8A, may represent an initially or previously mounted tool (hereinafter referred to as the "previous tool") or a tool mounted after the previous tool has been removed (hereinafter referred to as the "replacement tool").

Figure 8B:
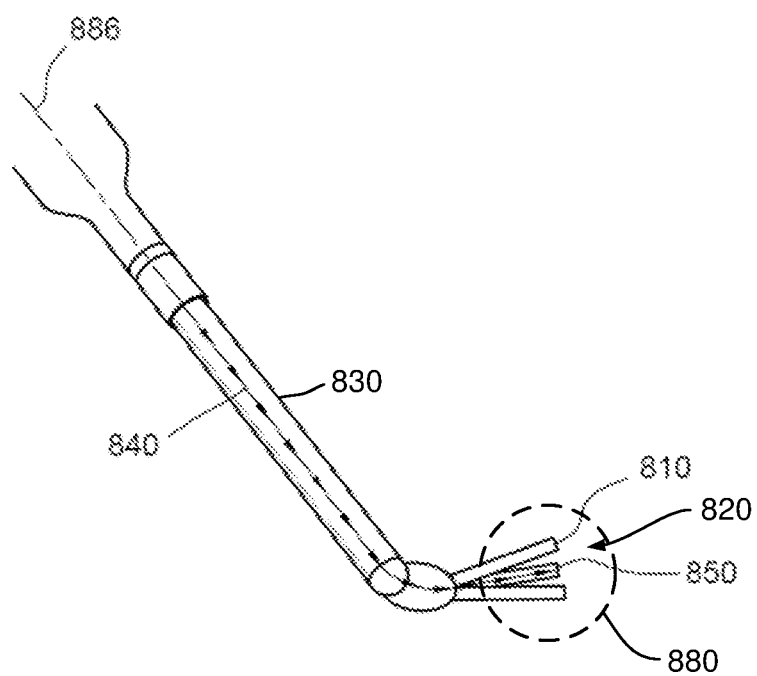
FIG. 8B schematically shows a previous tool and a superimposed replacement tool, in accordance with one or more embodiments.

Turning to FIG. 8B, a previous tool (810) and a replacement tool (850) are shown superimposed, with both tools in an operating configuration, e.g., inserted into the worksite (890) (e.g. comprising a surgical site in the body cavity, when considering a surgical scenario). The operating configuration may be commanded by a user based on a procedure for the previous tool (810) and/or the replacement tool (850). In FIG. 8B, the previous tool (810) is shown at an insertion location (820) prior to its removal, and the replacement tool (850) is shown at a target location after its insertion. The previous tool (810) and the replacement tool (850) may be similar or different. For example, the end effector of the replacement tool (850) may be of the same type as the end effector of the previous tool (810) (e.g., both tools may be equipped with a forceps type end effector), and the lengths of these end effectors may be the same or differ. Alternatively, the end effectors of the replacement and previous tools (850, 810) may be of different types (e.g., a forceps type end effector and a scalpel or electrocautery type end effector). The replacement tool (850) may also be the previous tool (810) itself, e.g., such as when the previous tool is removed for cleaning, reloading, inspection, etc. and then reinserted.

FIG. 8B also shows an insertion axis (886). The insertion axis (886) indicates possible translational movement of the previous/replacement tool along a prismatic joint of the tool holder carriage of the manipulator arm. In the example shown in FIG. 8B, the insertion axes of the previous tool (810) and the replacement tool (850) coincide because the configuration of the manipulator arm is unchanged. Those skilled in the art will understand that an insertion axis may also be provided by a combination of joints, such as a combination of rotary joints, that can be actuated to produce translational motion of a mounted tool.

FIG. 8B further shows an insertion trajectory (840). The insertion trajectory (840) may establish a path to be followed by one or more portions of the replacement tool (850), such as by a tip or by a central location of the end effector of the replacement tool (850), or by another specified portion of the replacement tool (850). The insertion trajectory (840) may, for example, extend centrally along a volume (830) occupied by the previous tool toward a target location (880). This volume may be known based on the geometry and kinematic configuration of the previous tool (810) prior to removal. By having a portion of the replacement tool (850), such as a tip or central part of the end effector (804), and/or another specified portion of the replacement tool (850), follow the insertion trajectory, the probability of unintentional interaction with other tools or other components present at the worksite (890) may be reduced. This is because the insertion trajectory may be defined to remain within a volume (830) previously occupied by the previous tool (810).

The target location (880) may be defined based on the insertion location (820). For example, the target location (880) may be defined as a location along a line segment connecting the insertion location (820) and a remote center of the previous tool, and may be at, or be a distance from, the insertion location (820); as a specific example, the target location (880) may be defined along such line segment and be 3 mm, 4 mm, 1 cm, etc. closer to the remote center than the insertion location (820). As another example, the target location (880) may be defined as a location along a central axis of the end effector of the previous tool (810), and may be at, or a distance from, the insertion location (820); as another specific example, the target location (880) may be defined along such central axis and be 3 mm, 4 mm, 1 cm, etc. closer to a proximal portion of the tool than the insertion location (820). A target location (880) selected in this manner would guide the replacement tool close to, but not all the way to, the insertion location (820).

In some embodiments, the target location (880) is further defined based on the kinematics of the replacement tool (850), and/or the allowed manipulator movements in controlling the replacement tool (850). Thus, the target location (880) may differ for replacement tools with different geometries, ranges of motion, and allowed manipulator movements, so that the target location set for each replacement tool is reachable by that replacement tool.

Consider as examples the two following scenarios. In both example scenarios, assume that the previous tool (810) before removal is bent from the shaft to the tip of the end effector, that the insertion location is at a tip of the previous tool (810) before removal, that the insertion trajectory is defined such that a tip of the replacement tool (850) follows a central axis of the previous tool (810) to the target location (880), and that a replacement tool (850) is equipped with an end effector shorter than the end effector of the previous tool (810). In both example scenarios, also assume that, if the previous tool (810) were reinserted as the replacement tool (850), the target location (880) would be set to be at a location along the central axis of the end effector of the previous tool (810) prior to the removal of the previous tool (810). Further, the target location would be set to be offset from the insertion location (820) by 3 mm toward a proximal portion of the previous tool (810) prior to removal.

In the first example, scenario (i), further assume that pivoting of the insertion axis (886) is not allowed in the insertion trajectory. In such a scenario (i), the shorter end effector of the replacement tool (850) would be unable to reach the same target location as a re-inserted previous tool (810). As a result, the target location (880) for the replacement tool (850) with the shorter end effector may be defined to be further from the insertion location (820) than the target location that would have been defined if the previous tool (810) was re-inserted as the replacement tool (850) (and be "short of" such re-inserted-previous-tool target location). In this example, the target location (880) may still be at a location along the central axis of the end effector of the previous tool (810), but in comparison to the target location (880) for reinsertion of the previous tool (810), the target location for the insertion of the replacement tool (850) may be even closer to the location of the proximal portion of the previous tool (810) prior to removal than the insertion location (820). In this way, the target location (880) defined is within reach of the end effector of the replacement tool (850), despite the replacement tool (850) being shorter than the previous tool (810). An example illustrating this scenario is provided below with reference to FIG. 12C.

Next, in a second example, scenario (ii), further assume that pivoting of the insertion axis (886) is allowed in the insertion trajectory of the replacement tool (850). In this scenario, the pivoting would allow the replacement tool with the shorter end effector to reach the target location that would have been set if the previous tool (810) was re-inserted as the replacement tool, although the shaft of the replacement tool (850) may not stay along the insertion trajectory. Accordingly, in this second scenario, the target location (880) for a replacement tool (850) with a shorter end effector can be defined to be the same as the target location if the previous tool (810) were to be re-inserted as the replacement tool (850). An example illustrating this scenario is provided below with reference to FIG. 12D.

The above examples can be analogized to cases where the range of motion for one or more degrees of freedom of the replacement tool (850) is insufficient to reach a target location that would have been set if the previous tool (810) was re-inserted as a replacement tool. The range of motion considerations may be based on physical range of motion constraints and/or based on software-imposed range of motion constraints. Examples of physical range of motion constraints include joint designs in the replacement tool (850) with greater or lesser joint range of motion for matching joints in the previous tool (810), and also include designs where the replacement tool (850) lacks a degree of freedom found in the previous tool (810). Thus, range of motion constraints may further be based on a complete absence of a degree of freedom that was available in the previous tool (810). Thus, in an example scenario where the replacement tool (850) is constrained by range of motion from reaching a target location that would have been defined if the previous tool (810) was re-inserted as a replacement tool, the target location may be defined differently (i.e., deviating from the target location that would be used for reinserting the previous tool) to allow the replacement tool (850) to reach the target location with its range of motion. An example illustrating this scenario is provided below with reference to FIG. 12E. Range of motion constraints may further also be associated with the manipulator arm carrying the previous tool or the replacement tool. Assume, for example, that the replacement tool (850) is considerably shorter than the previous tool (810) Accordingly, in order to reach a target location that would be used when reinserting the previous tool (810), the manipulator arm would have to participate in an insertion movement of the replacement tool (850) in order to compensate for the shorter replacement tool when performing the insertion. Participation of the manipulator arm may, however, not always be possible to the extent necessary, for example, when a joint of the manipulator arm itself reaches a range of motion limit, or due to a collision with another structure.

The target location (880) may be defined based on other factors instead of, or in addition to, the parameters described above. Example factors include a geometric cross-section of the replacement tool (850), a type of replacement tool (850) and associated use (e.g. energy tool, imaging tool, cutting tool, grasping tool, etc.), a goal of placing the replacement tool (850) closer to a center of a range of motion of one or more of its degrees of freedom, user preference, locations of other tools, locations of work pieces or worksites, anticipated location of the procedure to be carried out by the replacement tool (850), etc.

Other locations within the worksite may be selected as the target location (880) without departing from the disclosure. The target location (880) may, thus, be a point in space. The target location (880) may further include a tolerance. The tolerance may establish a target region which when reached by the end effector tip of the replacement tool (850) may indicate completion of the insertion. The tolerance may be selected based on accuracy requirements. If it is desired to precisely guide the replacement tool to a particular location, a narrow tolerance may be selected, whereas a wider tolerance may be selected for other scenarios.

As illustrated in FIG. 8B, the replacement tool (850), once completely inserted, may have a kinematic configuration similar to the previous tool (810). For end effectors of the same type and the same length, the kinematic configuration may be substantially identical, if the degrees of freedom of the replacement tool have a sufficient range of motion to achieve such similar kinematic configuration. In contrast, where the end effectors of the replacement and previous tools are of different length, or where the ranges of motion or degrees of freedom of the replacement and previous tools differ, the kinematic configuration may be similar but not identical, as further discussed above and with reference to FIG. 12A, FIG. 12B, FIG. 12C, FIG. 12 D, and FIG. 12E. A detailed discussion of the steps performed to replace a previous tool with a replacement tool are subsequently discussed with reference to FIG. 9, FIG. 10, and FIG. 11.

FIG. 9, FIG. 10, and FIG. 11 show flowcharts in accordance with one or more embodiments. The flowcharts of FIG. 9, FIG. 10, and FIG. 11 depict methods for a guided tool change, in accordance with one or more embodiments. One or more of the steps in FIG. 9, FIG. 10, and FIG. 11 may be performed by various components of the systems, previously described with reference to FIG. 1A, FIG. 1B, FIG. 2, FIG. 3, FIG. 4, FIG. 5, FIG. 6A, FIG. 6B, FIG. 6C, FIG. 6D, and FIG. 6E. These figures describe particular manipulator arms and particular tools, the manipulator arms and tools having certain degrees of freedom.

However, the subsequently described methods are not limited to a particular configuration of manipulator arms, tools and/or degrees of freedom. Instead, the methods are applicable to any type of manipulator arm, paired with any type of tool, used in any type of scenario.

While the various steps in these flowcharts are presented and described sequentially, one of ordinary skill will appreciate that some or all of the steps may be executed in different orders, may be combined or omitted, and some or all of the steps may be executed in parallel. Additional steps may further be performed. Furthermore, the steps may be performed actively or passively. For example, some steps may be performed using polling or be interrupt driven in accordance with one or more embodiments of the invention. By way of an example, determination steps may not require a processor to process an instruction unless an interrupt is received to signify that condition exists in accordance with one or more embodiments of the invention. As another example, determination steps may be performed by performing a test, such as checking a data value to test whether the value is consistent with the tested condition in accordance with one or more embodiments of the invention. Accordingly, the scope of the disclosure should not be considered limited to the specific arrangement of steps shown in FIG. 9, FIG. 10, and FIG. 11.

The flowchart of FIG. 9 may be understood as a main flowchart describing the steps associated with a guided tool change. FIG. 10 and FIG. 11 describe additional aspects of the guided tool change. Some of these additional aspects may or may not be included in a specific implementation of the guided tool change.

Turning to the flowchart of FIG. 9, a method for guided tool change, in accordance with one or more embodiments, is shown. A tool that is currently being used (hereinafter referred to as a previous tool) or has been used for a robotic procedure may be replaced by another tool (hereinafter referred to as a replacement tool), as subsequently described. The replacement may be performed such that the insertion of the replacement tool into the work site is guided; for example, one or more degrees of freedom (which may be different from the insertion degree of freedom) of the replacement tool and/or the manipulator arm to which the replacement tool is attached, are actuated to keep the replacement tool or a part of the replacement tool on an insertion trajectory. The guidance during the insertion may help facilitate quicker insertion or reduce the likelihood of unintended interaction of the replacement tool with the surrounding environment during the insertion. This may enable a quicker transition between previous tool and replacement tool for the operator. While the method may be performed to facilitate insertion of the replacement tool, a continuous insertion of the replacement tool is not necessary. For example, the insertion may be paused, or the replacement tool may even be retracted with or without being reinserted, while the subsequently discussed method ensures that the replacement tool is controlled to follow the insertion trajectory during insertion, retraction, and pausing of the insertion.

In Step 900, a determination is made whether a tool change is indicated in accordance with embodiments of the disclosure. Indications for a desired tool change may be, for example, a physical or virtual button being pressed by an operator or assistant, the previous tool being detached from the manipulator arm, or any other event defined as indicating a tool change. If a tool change is found to be indicated, then the execution of the method may proceed with Step 902.

In Step 902, the kinematic configuration of the manipulator arm and the previous tool is obtained in accordance with embodiments of the disclosure. The obtained kinematic configuration may include joint angles and/or positions of the previous tool when the previous tool is located at the insertion location. These joint angles and/or positions may enable a complete reconstruction of the kinematic configuration of the previous tool, when inserted in the worksite, at the insertion location. The position and/or orientation of the end effector of the previous tool (or any other component of the previous tool), or even a particular location on the previous tool (such as an end effector tip) may be reconstructed using the obtained kinematic configuration.

The obtaining of the kinematic configuration may be performed based on sensed joint states returned from the associated actuators (obtained, e.g., from incremental encoder signals, hall sensor signals, etc.). The obtained kinematic configuration may subsequently be stored in a memory, either immediately after the obtaining of the kinematic configuration, or at any time later, e.g., while the previous tool is still in place, or after the previous tool is removed.

In Step 904, a reference geometry of the previous tool is obtained in accordance with embodiments of the disclosure. Based on the reference geometry, an insertion trajectory for the insertion of the replacement tool may later be established. The reference geometry may include a series of line segments in a three-dimensional (3D) space, representing the recorded kinematic configuration of the previous tool. The line segments may have lengths corresponding to the links of the previous tool, and the angles between the line segments may be based on the previously recorded joint angles. Accordingly, the reference geometry may be established based on the kinematic configuration obtained in Step 902. The reference geometry may, additionally or alternatively, represent a volume occupied by the previous tool. The volume may be computed based on the line segments by establishing, for example, cylindrical volumes surrounding these line segments. The radii of the cylindrical volumes may be determined based on the width or diameter of the corresponding link of the previous tool. Non-cylindrical volumes may be used as well, for example to reflect a curvature of a link, a non-circular cross-section, etc. Alternatively, a 3D model of the previous tool may also be used to determine the volume. If a volume is used for the reference geometry, the volume may also be expanded or reduced based on other objectives such as improved safety or improved alignment etc., the volume may further be broadened to include the volume swept by the end effector as the previous tool is withdrawn from the worksite. Assume, for example, that the wrist of the previous tool (such as the tool shown in FIG. 6A and FIG. 6B) is flexed at the time of the removal. The wrist may remain flexed as the tool is withdrawn (until the wrist is forced straight when the end effector is entering the cannula). The volume swiped by the end effector may be deemed safe for an insertion of the replacement tool and may, thus, count toward the volume used for the reference geometry.

In Step 906, the removal of the previous tool is detected in accordance with embodiments of the disclosure. The removal, which may be performed by an assistant or operator, may be detected when the previous tool is mechanically separated from the manipulator arm. More specifically, the assistant or operator may mechanically disengage the tool from the manipulator arm and may further manually withdraw the disengaged tool from the work site. Consider, for example, a configuration of a manipulator arm as shown in FIG. 5 paired with a tool as depicted in FIG. 6A and FIG. 6B. The assistant or operator may disengage the tool by separating the tool from the tool holder carriage of the manipulator arm and withdraw the tool through the cannula of the manipulator arm. As the tool is withdrawn, the wrist of the tool, if flexed as shown in FIG. 6B, is straightened as it comes in contact with the cannula, thus allowing the end effector to pass through the cannula. As an alternative to the withdrawal of the previous tool from the insertion location by an assistant or operator, the withdrawal of the previous tool may also be performed by actuators of the robotic manipulation system. The previous tool may be withdrawn from the insertion location by the robotic manipulation system in a supervised or unsupervised manner. In this case, the robotic manipulation system may control the straightening of the wrist, as it reaches the cannula. The operator or assistant may eventually mechanically disengage the replacement tool from the manipulator arm, once the withdrawal of the previous tool has been completed by the robotic manipulation system.

In Step 908, the replacement tool is received, identified, and engaged in accordance with embodiments of the disclosure. Receiving the replacement tool may involve sensing the coupling of the replacement tool with the tool holder carriage of the manipulator arm. The replacement tool may be different from the previous tool, or it may be the previous tool being reinserted. If a replacement tool different from the previous tool is inserted, the geometry of the replacement tool may be different, the type and or number of degrees of freedom may be different, the range of motion available for the degrees of freedom may be different, and/or even the function(s) may be different (for example, the previous tool may be equipped with an end effector for cutting, whereas the replacement tool may be equipped with a forceps-type end effector or a single hook).

Once the installation of the replacement tool on the manipulator arm is detected, the replacement tool may be identified to obtain a kinematic description of the replacement tool. This kinematic description may include the link geometries, including shaft length, end effector length, type of end effector, a description of the wrist (if the replacement tool includes a wrist), and degrees of freedom of the replacement tool. The kinematic description may allow the configuration of the replacement tool in 3D space to be computed. Identifying the replacement tool may further involve obtaining additional parameters of the replacement tool. For example, gear ratios for driving the joints of the replacement tool may be obtained to enable calculation of joint movements of the replacement tool, given a mechanical input. The identification of the replacement tool may be performed based on information accompanying the replacement tool. For example, the replacement tool may include a readable memory chip from which the description and/or specifications of the replacement tool may be obtained. Alternatively, the description and/or specifications of the replacement tool may be provided by an operator or assistant.

Engaging the replacement tool may involve a mechanical engagement of the replacement tool with the tool holder carriage of the manipulator arm. The mechanical engagement may couple the degrees of freedom of the replacement tool to control inputs provided by the manipulator arm. For the previously described manipulator arms and tools (FIG. 5, FIG. 6A, FIG. 6B, FIG. 6C, FIG. 6D, and FIG. 6E), the control inputs may be mechanical inputs provided to spools that are rotatable to control cables actuating the degrees of freedom of the replacement tool. The tool holder carriage of the manipulator arm may include disks for coupling with the spools to drive the spools upon connection of the replacement tool to the manipulator arm. Once the replacement tool is engaged, the positions and/or orientations of all the joints of the replacement tool are known and controllable. In one or more embodiments, the engaging of the replacement tool may occur as the tool holder carriage is in a retracted position. The replacement tool may thus be engaged with the tool holder carriage without significantly protruding into the work site, through the cannula. For example, an engagement may be possible while the end effector of the replacement tool does not extend into the work site beyond the cannula. Subsequently, the engaged replacement tool may be inserted into the work site with the degrees of freedom of the replacement tool being controllable, as discussed below.

In Step 910, the insertion of the replacement tool toward the target location is facilitated, in accordance with embodiments of the disclosure. Joint angles or positions of the replacement tool (and/or of the manipulator arm) may be adjusted during insertion of the replacement tool. The insertion of the replacement tool may be driven by an external driving force applied, for example, by an operator or an assistant in accordance with embodiments of the disclosure. The driving force may be applied substantially in the direction of the insertion axis of the replacement tool. However, it may not be necessary for the driving force to be exactly aligned with the insertion axis. The degrees of freedom of the manipulator arm (with the exception of the insertion degree of freedom) may be position-controlled, thereby resisting movement that is not along the insertion axis. If a component of the external driving force in a direction not aligned with the insertion axis is excessive, visual, or auditory feedback may be provided to the operator or assistant, and/or further insertion of the replacement tool may be blocked. The acceptable limit of a deviation from the insertion axis may depend on various factors such as the current location on the insertion trajectory, the previous tool, the replacement tool, etc. As discussed below with reference to the flowchart of FIG. 10 and FIG. 11, an inaccurately applied driving force does not result in an inaccurately executed insertion of the replacement tool. The driving of the replacement tool by an external force is possible because one or more joints of the manipulator assembly are floating, as previously described.

In the example of the manipulator arm of FIG. 5, the prismatic joint enabling the linear movement of the tool holder carriage may be floating, thus providing the insertion degree of freedom allowing the insertion along the insertion axis by the external driving force. As the replacement tool is inserted, the elongate shaft of the replacement tool passes through the cannula as the end effector of the replacement tool approaches the target location. While the floating of a joint may primarily involve gravity compensation, additional physical characteristics may be superimposed. For example, a limit of the insertion speed may be imposed by superimposing a viscous friction.

In one or more embodiments, during the insertion of the replacement tool, the kinematic configuration of the replacement tool is controlled to facilitate the insertion. More specifically, one or more degrees of freedom of the replacement tool are actively controlled to make the replacement tool or a part of the replacement tool (for example an end effector tip or any other point on the replacement tool) follow the insertion trajectory toward the target location. In this scenario, only degrees of freedom of the replacement tool, but not degrees of freedom of the manipulator arm may be actuated to guide the replacement tool to move in accordance with the insertion trajectory. Additionally or alternatively, degrees of freedom of the manipulator arm may be controlled to make the replacement tool follow the insertion trajectory toward the target location. Only degrees of freedom of the manipulator arm may be actuated (manipulator arm controlled to make the replacement tool follow the insertion trajectory), or degrees of freedom of the manipulator arm and the replacement tool may be actuated (manipulator arm and replacement tool controlled to make the replacement tool follow the insertion trajectory). The method may, thus, control one or more degrees of freedom of the manipulator assembly in response to an external manipulation of the replacement tool. The one or more degrees of freedom being controlled may be different from the insertion degree of freedom. A detailed description of the control of one or more degrees of freedom to have the replacement tool move in accordance with the insertion trajectory is subsequently provided.

Turning to the flowchart of FIG. 10, in accordance with embodiments of the disclosure, a method for facilitating the insertion of the replacement tool toward the target location is described. The method of FIG. 10 is executed for the duration of the insertion.

In Step 1000, an insertion trajectory is determined in accordance with embodiments of the disclosure. In one or more embodiments, the insertion trajectory provides guidance during the insertion of the replacement tool. A tool tip of the replacement tool or any other element of the replacement tool may be controlled to be on the insertion trajectory, during the insertion.

The insertion trajectory may be based on the reference geometry of the previous tool and further on the kinematics and geometry of the replacement tool, in accordance with embodiments of the disclosure. Assume that the reference geometry includes a series of line segments representing the kinematic configuration of the previous tool, as previously described with reference to FIG. 9. These line segments may be used to construct the insertion trajectory. While the line segments of the reference geometry may have kinks representing sharper turns at the joints, the insertion trajectory derived from the line segments may contain such sharper turns, or be modified to have smooth transitions between the straight sections, thereby providing a trajectory with no discontinuities. As a result, the insertion trajectory may align, at least partially, with a central axis of the previous tool. The insertion trajectory may terminate at the target location. Alternatively, if the reference geometry of the previous tool is defined as a volume, the insertion trajectory may be established anywhere within that volume, e.g., to centrally track the volume toward the target location. The insertion trajectory may be selected to be entirely within the volume. As previously discussed with reference to FIG. 8B, the target location may or may not coincide with the insertion location of the previous tool, depending on the configuration of the system, user preference, the kinematics of the replacement tool, the allowance of manipulator motion to pivot the replacement tool, hardware and/or software constraints of the range of motion of one or more of the degrees of freedom of the replacement tool, any of the other factors described herein, etc. The insertion trajectory and target location may be defined accordingly.

The subsequently discussed steps may be performed during the insertion of the replacement tool in accordance with embodiments of the disclosure. However, a continuous insertion of the replacement tool is not necessary. For example, the insertion may be paused, or the replacement tool may even be retracted and reinserted, while the subsequently discussed steps are executed. The method may thus ensure that replacement tool follows the insertion trajectory under various conditions including insertion and retraction of the replacement tool.

In Step 1002, the current position of the replacement tool is determined in accordance with embodiments of the disclosure. More specifically, the location of the tool tip of the replacement tool or of another element of the replacement tool to be on the insertion trajectory may be determined. Forward kinematics based on the kinematic description of the replacement tool may be used to determine the current position of the replacement tool in space. The current position may be determined in any reference frame (e.g., in a Cartesian reference frame) that allows relating the current position to the insertion trajectory.

In Step 1004, a control command for the replacement tool to move in accordance with the insertion trajectory is determined, in accordance with embodiments of the disclosure. If the replacement tool deviates from the insertion trajectory, the control command may be selected to steer the replacement tool toward the insertion trajectory. If the replacement tool is on the insertion trajectory, the control command may be selected to keep the replacement tool on the insertion trajectory. The control command may be for one or more degrees of freedom of the replacement tool and/or the manipulator arm. In one embodiment of the disclosure, a point on the insertion trajectory is determined as the target point, toward which the replacement tool is to be driven. This target point may be selected based on the shortest distance between the replacement tool and the insertion trajectory (the shortest distance being defined by a line perpendicular to the insertion trajectory, and intersecting the replacement tool at the element of the replacement tool to be on the insertion trajectory). Using this target point, a control signal may be generated to adjust the one or more degrees of freedom of the replacement tool and/or the manipulator arm. In accordance with embodiments of the disclosure, the control signal may be generated as previously discussed with reference to FIG. 7, using inverse kinematics.

Depending on the degrees of freedom of the manipulator arm and the replacement tool, multiple possible control signals may be suitable, due to redundancies in the kinematic configuration of the manipulator arm and the replacement tool. To obtain the desired control signals, various kinematic constraints may be imposed to obtain a solution:

(i) In accordance with embodiments of the disclosure, the degrees of freedom available for control are degrees of freedom of the replacement tool. Referring to the examples for tools provided in FIG. 6A, FIG. 6B, FIG. 6C, FIG. 6D, and FIG. 6E, these degrees of freedom may include one or more rotational degrees of freedom at the wrist (e.g., wrist pitch, wrist yaw).

(ii) In accordance with embodiments of the disclosure, the degrees of freedom available for control include degrees of freedom of the manipulator arm (e.g., yaw, pitch of the tool holder carriage, and/or roll of the tool). The manipulator arm, when moving, effects a positional change of the replacement tool, thereby moving the replacement tool or a component of the replacement tool. In scenarios where the work site is a cavity, the movement of the manipulator may be constrained to establish a remote center of the manipulator arm, where only pivoting, but no translation other than along the insertion axis of the replacement tool is allowed. This remote center may coincide with the aperture where the tool enters the cavity, as illustrated in FIG. 8A. Through the pivoting of the tool shaft, the position of, for example, the end effector tip of the replacement tool may be updated when degrees of freedom of the manipulator arm are actuated. This approach may allow controlled insertion of a replacement tool even if the replacement tool is not equipped with a wrist (e.g., in case of an endoscope serving as the replacement tool).

(iii) In accordance with embodiments of the disclosure, combinations of (i) and (ii) may be implemented. The combination of (i) and (ii) may be applied when a replacement tool with an end effector shorter than the end effect of the previous tool, or a replacement tool with fewer degrees of freedom or lesser ranges of motion than the previous tool, is inserted. For example, it may not be possible for the shorter end effector to reach sufficiently close to the insertion location of the previous tool using wrist movement alone. In the described scenario, initially control of the degrees of freedom of the replacement tool may be sufficient to have the replacement tool follow the insertion trajectory. However, eventually when approaching the target location, movement of one or more degrees of freedom of the manipulator arm may be necessary to complete the insertion. Similarly, the combination of (i) and (ii) may be applied when a replacement tool with an end effector longer than the end effector of the previous tool is inserted, while in addition requiring the end effector of the replacement tool to have an orientation identical to the orientation of the previous tool. The "extra length" of the end effector of the replacement tool, in this scenario, may be accommodated by movement of one or more degrees of freedom of the manipulator arm. Various such scenarios are discussed below with reference to FIG. 12A, FIG. 12B, FIG. 12C, FIG. 12D, and FIG. 12E.

While the above description is based on an insertion trajectory, alternative methods for guiding the replacement tool may be used without departing from the disclosure. For example, a volume occupied by the previous tool (810) may be used to guide the replacement tool within that volume, may be used to define the insertion trajectory for the replacement tool, etc.

In Step 1006, in accordance with embodiments of the disclosure, at least one degree of freedom of the manipulator arm and the replacement tool is actuated based on the control command determined in Step 1004.

In Step 1008, a determination is made whether the target location has been reached by the replacement tool, in accordance with embodiments of the disclosure. If the target location has not been reached, then the execution of the method may return to Step 1002. Alternatively, if the target location has been reached, then the execution of the method may proceed with Step 1010. For the purpose of executing Step 1008, the target location may be spatially expanded to form a target region with a non-zero geometric extent. The size of the target region may be determined based on safety and accuracy considerations. The target region may be, for example, a spherical region centrally surrounding the target location.

In Step 1010, further insertion of the replacement tool is impeded in accordance with embodiments of the disclosure. A virtual wall with an appropriate level of stiffness may block or otherwise hinder further insertion movement on the joint that is controlled as floating. Accordingly, while retraction may still be possible, further insertion is not possible unless the external force overcomes the resistance force of the actuators providing the virtual wall. A visual, auditory and/or haptic cue may further be provided to the operator. Alternatively, the floating joint may be switched to a velocity or position control mode, thus impeding further movement.

After completion of Step 1010, the insertion of the replacement tool is deemed completed.

To further illustrate the steps of the method of FIG. 10, these steps are subsequently discussed with reference to the scenario shown in FIG. 8B. Assume that the insertion axes (886) of the previous tool and the replacement tool coincide. The linear degree of freedom of the tool holder carriage is floating, and accordingly an externally applied force results in an insertion of the replacement tool toward the target location. Initially, the end effector of the replacement tool is on the insertion axis. Assume that the end effector tip is the element of the replacement tool to be controlled on the insertion trajectory. Accordingly, for the initial straight portion of the insertion trajectory, no significant actuation of the degrees of freedom of the replacement tool is necessary, and the end effector of the replacement tool being inserted advances straight on the insertion trajectory. Upon reaching the curved section of the insertion trajectory, in Step 1004, a deviation of the end effector tip from the insertion trajectory is detected in accordance with embodiments of the disclosure. The actuation to keep the end effector tip on the insertion trajectory is determined to be a flexing of the tool wrist. No other actuation of degrees of freedom is necessary, and the insertion axis, therefore, proceeds straight. In Step 1006, the wrist joint is actuated, and the end effector tip, therefore, remains on the insertion trajectory. Repetition of Steps 1004 and 1006 incrementally adjust the wrist as the insertion progresses in accordance with embodiments of the disclosure. Eventually, once the target location is reached by the end effector tip, the execution of the method terminates.

While the above scenario provides one basic example, additional scenarios are discussed below with reference to FIG. 12A, FIG. 12B, FIG. 12C, FIG. 12D, and FIG. 12E. Those skilled in the art will appreciate that the described methods may be applied to other scenarios, not shown here. These additional scenarios also discuss the consequences of a changing end effector length, allowing pivoting of the insertion axis, etc. in accordance with embodiments of the disclosure.

Turning to the flowchart of FIG. 11, in accordance with embodiments of the disclosure, a method for facilitating insertion of the replacement tool toward the target location is described. The method of FIG. 11 may be executed as an alternative to the method of FIG. 10. Unlike the method of FIG. 10, the method described below provides an intuitive force feedback to the operator or assistant driving the insertion movement of the tool in accordance with embodiments of the disclosure. This force feedback may be particularly beneficial in scenarios that involve joint movement of the manipulator arm joints, during the insertion. To further show the benefit, consider the scenario depicted in FIG. 8A and FIG. 8B, in which the movement of the replacement tool inside a cavity is not visible to the assistant driving the insertion movement of the replacement tool. If reconfiguration of the manipulator joints is used to keep the replacement tool on the insertion trajectory, this manipulator joint movement may surprise the assistant. Further, as the manipulator arm joints move, the direction of the insertion movement itself changes, thereby directly affecting the interaction of the assistant with the manipulator arm during the insertion. The described method may provide an intuitive force feedback to the assistant, thus facilitating the insertion, in particular when manipulator arm joint movements are involved in the insertion. The method relies on a virtual manipulator assembly used for controlling the physical manipulator assembly (the physical manipulator assembly including the replacement tool and one or more manipulator arm segments or links). In accordance with embodiments of the disclosure, the virtual manipulator assembly while being constrained to a constraint trajectory, is configured to follow the movement of the physical manipulator assembly. The virtual manipulator assembly may not exactly follow the physical manipulator assembly, due to being constrained by the constraint trajectory. The resulting deviations between the virtual and physical manipulators may be used to generate spring-like forces presented to the assistant performing the insertion movement, the spring-like forces correcting the movement of the physical manipulator assembly toward the movement of the virtual manipulator assembly. The subsequently described steps implement this paradigm.

In Step 1100, a constraint trajectory is determined in accordance with embodiments of the disclosure. The constraint trajectory, analogous to the insertion trajectory introduced in FIG. 10, may be used to provide guidance during the insertion of the replacement tool. Accordingly, Step 1100 may be performed analogous to Step 1000.

The following steps may be performed during the insertion of the replacement tool. However, a continuous insertion of the replacement tool is not necessary. For example, the insertion may be paused, or the replacement tool may even be retracted and reinserted, while the subsequently discussed steps are executed. The method may thus ensure that replacement tool follows the insertion trajectory under various conditions including insertion and retraction of the replacement tool.

In Step 1102, a current kinematic configuration of a virtual manipulator assembly is determined in accordance with embodiments of the disclosure. The current kinematic configuration of the virtual manipulator assembly may be obtained by updating a prior (obtained from execution of the method of FIG. 11 at the previous time step) kinematic configuration of the virtual manipulator assembly. To initially set the kinematic configuration of the virtual manipulator assembly, e.g., at the time when the replacement tool is engaged, the kinematic configuration of the virtual manipulator assembly may be set to match the kinematic configuration of the physical manipulator assembly. The current kinematic configuration of the virtual manipulator assembly may be determined in three steps.

In a first step (Step 1102A), an energy minimization is performed in accordance with embodiments of the disclosure. The energy minimization results in a first set of joint angle corrections to be applied to the kinematic configuration of the virtual manipulator assembly of the previous time step. The first set of joint angle corrections may get the virtual manipulator assembly (or more specifically, an element of the virtual manipulator arm assembly such as the end effector tip (which can be defined to be a reference point)) close to but not necessarily on the constraint trajectory. In a second step (Step 1102B), a second set of joint angle corrections, to be applied to the kinematic configuration of the virtual manipulator assembly of the previous time step, is obtained in accordance with embodiments of the disclosure. The second set of joint angle corrections may translate the virtual manipulator assembly onto the constraint trajectory, after the first set of joint angel corrections drove the virtual manipulator assembly close to the constraint trajectory. In a third step (Step 1102C), the first and the second set of joint angle corrections are applied to the kinematic configuration of the virtual manipulator assembly of the previous time step in accordance with embodiments of the disclosure. The three steps are subsequently described.

In Step 1102A, in accordance with embodiments of the disclosure, an energy optimization is performed on a joint level, as the current configurations of the virtual manipulator assembly and the physical manipulator assembly deviate. Specifically, an energy buildup may be related to the proportional control gains of the joint controllers attempting to minimize an error between the current configurations of the virtual manipulator assembly and the physical manipulator assembly, when the kinematic configuration of the virtual manipulator assembly serves as the control input to the joint controllers. By optimizing the joint angles of the virtual manipulator assembly, the energy buildup in the joints may be minimized. The optimization may be performed as follows.

First, the point on the constraint trajectory closest to the element of the virtual manipulator assembly to be kept on the constraint trajectory (which can be defined to be a reference point), $X_{virt.\ manipulator\ assembly}$, is identified. Next, a tangent is obtained at the identified point on the constraint trajectory. These operations are performed in Cartesian space.

Subsequently, the obtained tangent is converted to the joint space, using the inverse Jacobian, which allows optimization of the joint angles of the virtual manipulator assembly for the purpose of the energy minimization. A first set of joint angle corrections, $d\Theta_{energy}$ for the virtual manipulator assembly may thus be obtained using any type of optimization method. $d\Theta_{energy}$ may minimize the energy for the combination of all joints under consideration based on the discrepancies between the joint angles of the physical and virtual manipulator assemblies and the associated proportional control gains. Note that $d\Theta_{energy}$ may put the element of the virtual manipulator assembly to be kept on the constraint trajectory (reference point) near the constraint trajectory, but not necessarily on the constraint trajectory, as a result of performing the optimization using a tangent rather than the constraint trajectory itself. The subsequently performed Step 1102B identifies a second set of joint angle corrections that put the element of the virtual manipulator assembly to be kept on the constraint trajectory (reference point) onto the reference trajectory.

In Step 1102B, in accordance with embodiments of the disclosure, a second set of joint angle corrections that translates the virtual manipulator assembly onto the constraint trajectory is determined using the following operations.

First, the point on the constraint trajectory closest to the element of the virtual manipulator assembly to be kept on the constraint trajectory (which can be defined to be a reference point), $X_{virt.\ manipulator\ assembly}$, after adjustment using $d\Theta_{energy}$ (converted to the Cartesian reference frame), $X_{virt.\ manipulator\ assembly\ +}$ is identified. Next, the corrective movement toward the point on the constraint trajectory is obtained in Cartesian space. The corrective movement may be obtained by subtracting $X_{virt.\ manipulator\ assembly\ +}$ from the point on the constraint trajectory closest to the element of the virtual manipulator assembly to be kept on the constraint trajectory after adjustment using $d\Theta_{energy}$. The obtained corrective movement is subsequently translated to joint space to obtain a second set of joint angle corrections $d\Theta_{translate}$ for the virtual manipulator assembly.

In Step 1102C, the element of the virtual manipulator assembly to be kept on the constraint trajectory (which can be defined to be a reference point) is updated based on: $\Theta_{virt.\ manipulator\ assembly}(t+1)=\Theta_{virt.\ manipulator\ assembly}(t)+\beta\ d\Theta_{energy}+\gamma\ d\Theta_{translate}$, with $0<\beta<1$ and $0<\gamma<1$ to limit the magnitude of the corrective movements for stability reasons. After completion of Step 1102C, a kinematic configuration of the virtual manipulator assembly on the constraint trajectory, is available.

In the above described Steps 1102A and 1102B, multiple forward and inverse kinematics transformations are performed to perform steps in Cartesian space and in joint space. While an updated Jacobian may be computed separately for each step, a single Jacobian may be used for these steps. The loss in accuracy may be negligible, whereas the computational efficiency may increase substantially.

In Step 1104, the actuators of the physical manipulator assembly are driven using the current kinematic configuration of the virtual manipulator assembly in accordance with embodiments of the disclosure. Assume that the joint controllers are PD controllers. The use of the joint angles of the virtual manipulator assembly as the control inputs to the corresponding joint controllers effectively establishes springs in these joints: the higher the discrepancy between the joint angles of the virtual manipulator assembly and the joint angles of the physical manipulator assembly, the stronger the torques produced by the corresponding joint actuators. The torques produced by the joints of the physical manipulator assembly may be experienced by the assistant driving the insertion movement. The assistant thus obtains feedback regarding the discrepancy in an intuitive manner.

The assistant may allow the corrective movement, caused by the force buildup in the actuators, to happen, and as a result the discrepancy is reduced. On the other hand, if the user is preventing the corrective movement from occurring (by producing a counterforce), the force buildup in the actuators may persist or may even increase, if the discrepancy further increases. If the discrepancy increases beyond a previously set level, a visual or acoustic warning may be issued, and/or the execution of the method of FIG. 11 may be stopped.

In Step 1106, a determination is made whether the target location has been reached by the replacement tool. If the target location has not been reached, then the execution of the method may return to Step 1102. Alternatively, if the target location has been reached, then the execution of the method may proceed with Step 1108. For the purpose of executing Step 1106, the target location may be spatially expanded to form a target region with a non-zero geometric extent. The size of the target region may be determined based on safety and accuracy considerations. The target region may be, for example, a spherical region centrally surrounding the target location.

In Step 1108, further insertion of the replacement tool is impeded. A soft or hard virtual wall may block further insertion movement on the joint that is controlled as floating. Accordingly, while retraction may still be possible, further insertion is not possible unless the external force overcomes the resistance force of the actuators providing the virtual wall. Alternatively, the floating joint may be switched to a velocity or position control mode, thus impeding further movement.

After completion of Step 1108, the insertion of the replacement tool is deemed to be completed.

As previously noted, the method of FIG. 11 may be particularly useful when applied to degrees of freedom that are responsible for an interaction with the assistant. In the example of the manipulator arm introduced in FIG. 5, these degrees of freedom may include yaw, pitch and IO movement of the tool holder carriage. When, during the insertion, one or more of these degrees of freedom of the physical manipulator assembly deviate from the corresponding degrees of freedom of the virtual manipulator assembly (e.g., due to an excessive force not aligned with the insertion axis applied by the operator), the constraint trajectory may, nevertheless, be followed, based on the physical manipulator assembly being controlled to achieve the configuration of the virtual manipulator assembly. Those skilled in the art will appreciate that the method is applicable to any other type of manipulator arm/manipulator arm assembly, without departing from the disclosure.

When the described method is used for controlling yaw, pitch, and IO degrees of freedom of the manipulator arm segment supporting the tool (e.g. the tool holder carriage), these degrees of freedom need to move under consideration of the one or more tool degrees of freedom (e.g., a pivoting of the wrist) to compensate for a translation that is introduced by the movement of the tool degree(s) of freedom. Accordingly, previously described Step 1102A may be implemented as follows.

For the three degrees of freedom (yaw, pitch, and IO) of the tool holder carriage, and using a to indicate motion along the constraint trajectory (as previously described with reference to FIG. 11), $$v_{jnt} = \frac{d\theta}{dx}\frac{dx}{d\alpha} = J_{3x3}^{-1} v_{cart}$$

may be used for the conversion of the tangent in Cartesian space to joint space, in preparation for performing the energy minimization of Step 1102A. Here, wan is a Cartesian velocity representing the constraint trajectory in Cartesian space, $v_{jnt}$ is obtained by transforming $v_{cart}$ into the joint space, and $J_{3\times3}^{-1}$ is the inverse Jacobian used for the transformation. When separating $\Theta$ into $\Theta_{tool}$ (for the tool degrees of freedom) and $\Theta_{carriage}$ (for the tool holder carriage degrees of freedom), the conversion of the tangent in Cartesian space to joint space may instead be performed using $$v_{jnt} = \frac{d\theta_{carriage}}{dx}\frac{dx}{d\alpha} - \frac{d\theta_{carriage}}{dx}\frac{dx}{d\theta_{tool}}\frac{d\theta_{tool}}{d\alpha} = J_{3\times3}^{-1}v_{cart} - J_{3\times3}^{-1}J_{trans\times tool}\frac{d\theta_{tool}}{d\alpha},$$

where $J_{trans\times tool}$ is the portion of J that maps tool degrees of freedom to translation, and $d\Theta_{tool}/d\alpha$ is a function of the algorithm for guiding the end effector during the insertion, as previously described. The energy minimization of Step 1102A and all other steps of the method of FIG. 11 may then be completed as previously described.

Additional functionalities may be combined with the methods described in FIG. 9, FIG. 10, and FIG. 11. At least some of these features may further increase the safety of the insertion, as subsequently discussed.

In accordance with embodiments of the disclosure, the insertion of the replacement tool may be at least partially monitored by an assistant or an operator, using an imaging device. Consider the scenario of FIG. 8A and FIG. 8B, in which the main movements of the tool during the insertion are (a) a linear insertion, and (b) a flexion of the wrist to pivot the end effector. As governed by the insertion trajectory, the flexing of the wrist occurs toward the end of the insertion movement. Assume that an imaging device is available. To benefit from the availability of the imaging device, the methods of FIG. 9, FIG. 10, and FIG. 11 may be modified to incorporate information obtained from the imaging device. Specifically, the stage of the insertion that requires flexion of the wrist may only be allowed when the end effector is known to be within the field of view of the imaging device. The field of view may be calculated using the kinematics of the manipulator arm that supports the imaging device, and the optical characteristics of the imaging device. If the instrument is not within the field of view, further insertion of the replacement tool may be impeded as described in Steps 1010 and 1112. Additionally, a manual confirmation by the assistant observing the insertion by viewing the video image obtained from the imaging device may be required to allow completion of the insertion.

In accordance with embodiments of the disclosure, a sensing of the insertion force is performed to monitor the insertion. An excessive insertion force may indicate that an obstacle is blocking further insertion. To prevent potential damage to the obstacle or tool, further insertion of the replacement tool may be impeded as described in Steps 1010 and 1112 when an excessive insertion force is detected. The force sensor(s) to be used for the force sensing may be configured to measure the insertion force at the tip of the end effector, or in any other desirable region on the tool or on the manipulator arm.

In accordance with embodiments of the disclosure, a periodically updated visual rendering of the insertion is provided to the assistant performing the insertion. The visual rendering may visualize aspects of the insertion that may otherwise be invisible, such as movement of degrees of freedom of the replacement tool, including flexion of the wrist of the tool, e.g., inside a cavity. The visual rendering may include a rendering of the insertion trajectory and a rendering of the replacement tool as it travels along the insertion trajectory. Further, a volume of the previous tool may be rendered. The rendering of the replacement tool may be based on the actual kinematics of the replacement tool being inserted. Accordingly, deviations from the insertion trajectory may be visualized, for example, when the assistant, while inserting the replacement tool, exerts an excessive force on the manipulator arm in a direction not aligned with the insertion axis, thus causing a misalignment of the manipulator arm and/or the replacement tool.

In one or more embodiments, additional constraints may be imposed on the joint(s) providing the insertion degree of freedom. While the joint(s) were previously described as floating, a ratcheting characteristic may be superimposed. The ratcheting may limit the floating to the insertion direction by reducing or otherwise impeding movement in the opposite direction. The ratcheting may be extended to apply to the tool shaft of the replacement tool as well, if the insertion of the replacement tool involves pivoting of the tool shaft.

Turning to FIG. 12A, FIG. 12B, FIG. 12C, FIG. 12D, and FIG. 12E, various outcomes of the insertion of replacement tools using the methods of FIG. 9, FIG. 10, and FIG. 11, in accordance with one or more embodiments, are schematically shown. Each of FIG. 12A, FIG. 12B, FIG. 12C, FIG. 12D, and FIG. 12E show the previous tool at the insertion location prior to the removal, the replacement tool when fully inserted to the target location, and the tool tips or end effectors of the previous tool and the replacement tool. In each scenario, the end effector of the previous tool is flexed relative to the shaft of the replacement tool (i.e., not forming a straight extension of the shaft). Accordingly, the end effector of the replacement tool may also require some degree of flexion. The scenarios reflect the configuration initially introduced in FIG. 8A, where a tool enters a worksite through an aperture. The mechanical features shown of the tool are an elongate shaft and an end effector. A wrist joint pivotally couples the end effector to the elongate shaft. For simplicity, in the depictions of FIG. 12A, FIG. 12B, FIG. 12C, 12D, and FIG. 12E, a single degree of freedom at the wrist is assumed. Simplifying assumptions are made as pointed out separately for each of the subsequently discussed examples. Those skilled in the art will recognize that the methods described in FIG. 9, FIG. 10, and FIG. 11 are not limited to the scenarios shown in FIG. 12A, FIG. 12B, FIG. 12C, 12D, and FIG. 12E.

Figure 12A:
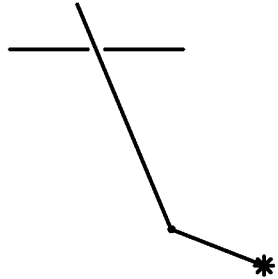
FIG. 12A, FIG. 12B, FIG. 12C, FIG. 12D, and FIG. 12E show various outcomes of the insertion of replacement tools using the methods shown and described in regard to FIG. 9, FIG. 10, and FIG. 11, in accordance with one or more embodiments.

In FIG. 12A, the replacement tool and the previous tool include end effectors of identical lengths. For simplicity, assume that the location of the tool tip of the previous tool serves as the target location. Accordingly, after the completed insertion, when the replacement tool has reached the target location in various embodiments, the kinematic configuration of the replacement tool is identical to the kinematic configuration of the previous tool. The insertion depth and insertion orientations of the shaft of the previous tool and the replacement tool are identical or near-identical. Further, the wrist angles and the locations of the tool tips of the replacement tool and the previous tool coincide.

Figure 12B:
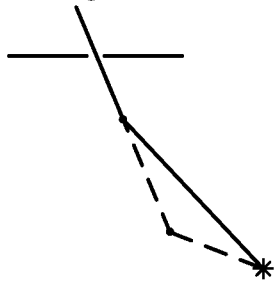

In FIG. 12B, the replacement tool is equipped with an end effector that is longer than the end effector of the previous tool. For simplicity, assume that the location of the tool tip of the previous tool serves as the target location. Due to the extra length of the end effector of the replacement tool, the locations of the replacement tool tip and the previous tool tip still coincide after completed insertion of the replacement tool toward the target location, in various embodiments. However, the kinematic configuration differs. Specifically, the wrist angle of the replacement tool is less than the wrist angle of the previous tool to reach the same tool tip location. Further, the insertion depth of the shaft of the replacement tool is less than the insertion depth of the shaft of the previous tool. Despite the different kinematic configurations, the insertion is conducted to keep the tool tip of the replacement tool on the insertion trajectory throughout the insertion. Accordingly, during the insertion, the wrist of the replacement tool is maintained in an extended configuration until the tool tip reaches the wrist location of the previous tool, where the wrist of the replacement tool begins to flex to keep the tool tip of the replacement tool on the insertion trajectory. Simple and efficient insertion is thus provided, despite a change in end effector length.

Figure 12E:
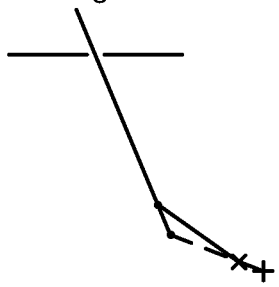
Figure 12C:
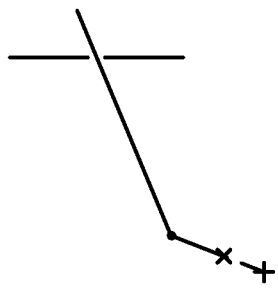

In FIG. 12C, the replacement tool is equipped with an end effector that is shorter than the end effector of the previous tool. Due to the reduced length of the end effector and degree of freedom constraints (the orientation of the tool shaft is held constant), the target location is selected "short of" the tool tip location of the previous tool. After the completed insertion, when the replacement tool has reached the target location in various embodiments, the kinematic configuration of the replacement tool is identical to the kinematic configuration of the previous tool, with the exception of the shorter end effector.

FIG. 12A, FIG. 12B, and FIG. 12C have in common that only the wrist configuration is changed during the insertion, whereas the orientation of the tool shaft is kept constant.

Figure 12D:
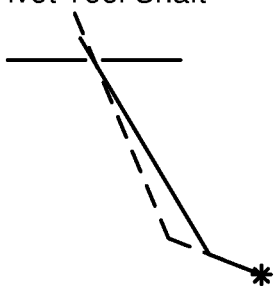

In FIG. 12D, the replacement tool is equipped with an end effector that is shorter than the end effector of the previous tool, similar to the scenario described in FIG. 12C. However, in FIG. 12D, not only the wrist configuration, but also the tool shaft orientation is changed during the insertion. More specifically, in FIG. 12D, a pivoting of the tool shaft about a remote center of the manipulator arm coinciding with the aperture, where the replacement tool enters the worksite, is allowed. The combination of wrist flexion and tool shaft pivoting enables the tool tip of the replacement tool to reach the location of the tool tip of the previous tool, despite the shortened end effector. During the insertion, the wrist of the replacement tool is maintained in an extended configuration until the tool tip reaches the wrist location of the previous tool, where the wrist of the replacement tool begins to flex to keep the tool tip of the replacement tool on the insertion trajectory. To reach the target location which, for simplicity is selected to coincide with the location of the tool tip of the previous tool, eventually a shaft pivoting is performed in coordination with the wrist flexion, until the tool tip of the replacement reaches the target location, while always remaining on the insertion trajectory. Depending on the geometry of the insertion trajectory, including radii at transitions between straight sections of the insertion trajectory, the pivoting may be gradually phased in and phased out to obtain smooth coordinate movement between the shaft pivoting and the wrist flexion. Simple and efficient insertion is thus provided, despite a change in end effector length.

The coordinated pivoting of the shaft and the wrist flexion may also be used when the replacement tool is equipped with an end effector that is longer than the end effector of the previous tool, such as in the scenario of FIG. 12B. Here, the tool tip of the replacement tool may reach a target location coinciding with the tool tip of the previous tool, while also having the end effector orientation of the replacement tool match the end effector orientation of the previous tool.

In the scenarios shown in FIGS. 12A, 12B, 12C, and 12D, the degrees of freedom of the replacement tool have a sufficient range of motion to achieve the illustrated kinematic configurations. For example, in FIG. 12A, the range of motion of the wrist of the replacement tool is sufficient to achieve the wrist configuration of the previous tool. In other scenarios, the replacement tool may have a limited range of motion, or one or more degrees of freedom may be entirely unavailable, for example when a previous tool with a wrist is replaced by a replacement tool without a wrist. In such scenarios and for some embodiments, the described methods would rely on shaft pivoting to compensate for the limited range of motion at the wrist.

In FIG. 12E, the replacement tool is equipped with an end effector that has a length similar to the end effector of the previous tool. However, the wrist of the replacement tool has a limited range of motion, in comparison to the wrist of the previous tool. When not allowing pivoting of the shaft, the tool tip of the replacement tool, therefore, is unable to reach a target location coinciding with the location of the tool tip of the replacement tool. Accordingly, the target location is selected "short of" the tool tip location of the previous tool.

However, as previously noted, when allowing the shaft to pivot, the limited range of motion at the wrist of the replacement tool may be compensated for by the pivoting of the shaft, enabling the end effector of the replacement tool to reach the location of the previous tool tip, despite the shortened end effector.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A computer-assisted medical system comprising:
   a manipulator arm; and
   a controller comprising a computer processor and configured to:
     determine a kinematic configuration, the kinematic configuration being prior to an installation of a replacement tool on the manipulator arm, and the kinematic configuration being of the manipulator arm and a previous tool attached to the manipulator arm and with an end effector of the previous tool located at an insertion location,
     determine a reference geometry of the previous tool in the kinematic configuration,
     determine a partially non-straight insertion trajectory for the replacement tool based on the reference geometry, and
     control the replacement tool to move in accordance with the insertion trajectory while the replacement tool is inserted toward a target location of the insertion trajectory; wherein:
       to control the replacement tool to move in accordance with the insertion trajectory, the controller is configured to: control a joint of the replacement tool to alter an angle or position of the joint such that the end effector follows the partially non-straight insertion trajectory.

2. The computer-assisted medical system of claim 1, wherein the previous tool and the replacement tool are the same tool.

3. The computer-assisted medical system of claim 1, wherein the insertion location is a location of a tool tip of the previous tool in the kinematic configuration, and wherein the target location is based on the insertion location.

4. The computer-assisted medical system of claim 1, wherein the controller is further configured to:
- impede further insertion of the replacement tool past the target location; or
- impede movement of the replacement tool in response to the replacement tool reaching the target location.

5. The computer-assisted medical system of claim 1, wherein the manipulator arm and the replacement tool together have a plurality of degrees of freedom, and wherein controlling the replacement tool to move in accordance with the insertion trajectory results in an actuation of at least one degree of freedom of the plurality of degrees of freedom other than an insertion degree of freedom.

6. The computer-assisted medical system of claim 1, wherein controlling the angle or position of the joint of the replacement tool comprises a flexing of a wrist between a shaft and an end effector of the replacement tool.

7. The computer-assisted medical system of claim 6, wherein the controller is further configured to:
- determine whether the end effector of the replacement tool is in a field of view of an imaging device; and
- allow the flexing of the wrist only when the end effector of the replacement tool is visible in the field of view.

8. The computer-assisted medical system of claim 1, wherein the controller is further configured to:
- sense an insertion force of the replacement tool; and
- impede further insertion of the replacement tool in response to the insertion force exceeding a threshold.

9. The computer-assisted medical system of claim 1, wherein the controller is further configured to:
- obtain a kinematic description of the replacement tool; and
- determine the insertion trajectory further based on the kinematic description.

10. The computer-assisted medical system of claim 9, wherein the controller is configured to determine the insertion trajectory further based on the kinematic description by:
- determining the insertion trajectory further based on a length of an end effector of the replacement tool relative to a length of the end effector of the previous tool.

11. The computer-assisted medical system of claim 9, wherein the kinematic description of the replacement tool specifies a range of motion of a degree of freedom of the replacement tool, and
wherein the controller is configured to determine the insertion trajectory further based on the range of motion of the degree of freedom of the replacement tool.

12. The computer-assisted medical system of claim 1, wherein controlling the replacement tool to move in accordance with the insertion trajectory comprises controlling an end effector tip of the replacement tool to follow the insertion trajectory, and wherein the insertion trajectory comprises a curved section.

13. The computer-assisted medical system of claim 1, wherein the insertion trajectory comprises a line segment, wherein the line segment aligns with a central axis of the previous tool in the kinematic configuration, and wherein controlling the replacement tool to move in accordance with the insertion trajectory comprises controlling a point on the replacement tool to remain on the line segment.

14. The computer-assisted medical system of claim 1, wherein:
- the reference geometry comprises a first line segment and a second line segment, and wherein determining the insertion trajectory comprises establishing a smooth transition between the first and second line segments; or
- the reference geometry is based on a volume occupied by the previous tool, and wherein determining the insertion trajectory comprises defining the insertion trajectory entirely within the volume occupied by the previous tool.

15. The computer-assisted medical system of claim 1, wherein determining the insertion trajectory based on the reference geometry comprises: reversing a removal trajectory of the previous tool.

16. The computer-assisted medical system of claim 1, wherein the controller is configured to determine the insertion trajectory such that, in response to the end effector of the previous tool being flexed relative to a shaft of the previous tool and the replacement tool comprising a wrist and an end effector, the end effector of the replacement tool being longer than the end effector of the previous tool,
upon completion of the insertion of the replacement tool toward the target location:
- an orientation of a shaft of the replacement tool coincides with an orientation of the shaft of the previous tool,
- an insertion depth of the shaft of the replacement tool is less than an insertion depth of the previous tool, and
- a wrist angle of the wrist of the replacement tool is less than an angle of the end effector of the previous tool relative to the shaft of the previous tool.

17. The computer-assisted medical system of claim 1, wherein the controller is configured to determine the insertion trajectory such that, in response to the end effector of the previous tool being flexed relative to a shaft of the previous tool and the replacement tool comprising a wrist and an end effector, the end effector of the replacement tool being shorter than the end effector of the previous tool,
upon completion of the insertion of the replacement tool toward the target location:
- an orientation of a shaft of the replacement tool coincides with an orientation of the shaft of the previous tool,
- an insertion depth of the shaft of the replacement tool coincides with an insertion depth of the previous tool,
- a wrist angle of the wrist of the replacement tool equals an angle of the end effector of the previous tool relative to the shaft of the previous tool.

18. The computer-assisted medical system of claim 1, wherein the controller is configured to determine the insertion trajectory such that, in response to the end effector of the previous tool being flexed relative to a shaft of the previous tool and the replacement tool comprising a wrist and an end effector, the end effector of the replacement tool being shorter than the end effector of the previous tool,
upon completion of the insertion of the replacement tool toward the target location:
- a shaft of the replacement tool is pivoted relative to the shaft of the previous tool.

19. The computer-assisted medical system of claim 1, wherein the controller is further configured to:
- facilitate a retraction of the replacement tool by controlling the replacement tool to move in accordance with a reversal of the insertion trajectory in response to the retraction of the replacement tool.

20. A method for operating a medical system, comprising:
determining a kinematic configuration, the kinematic configuration being of a manipulator arm and a previous tool attached to the manipulator arm and with an end effector of the previous tool inserted at an insertion location;
determining a reference geometry of the previous tool in the kinematic configuration;
detecting a removal of the previous tool from the manipulator arm;
detecting an installation of a replacement tool on the manipulator arm;
determining a partially non-straight insertion trajectory for the replacement tool based on the reference geometry; and
controlling the replacement tool to move in accordance with the insertion trajectory while the replacement tool is inserted toward a target location of the insertion trajectory,
wherein the controlling the replacement tool to move in accordance with the insertion trajectory comprises the controlling is configured to: control a joint of the replacement tool to alter an angle or position of the joint such that the end effector follows the partially non-straight insertion trajectory.

21. The method of claim 20, further comprising:
impeding further insertion of the replacement tool past the target location; or
impeding movement of the replacement tool in response to the replacement tool reaching the target location.

22. The method of claim 20, wherein the controlling the replacement tool to move in accordance with the insertion trajectory results in an actuation of at least one degree of freedom of the manipulator arm other than an insertion degree of freedom.

23. The method of claim 20, further comprising:
obtaining a kinematic description of the replacement tool; and
determining the insertion trajectory further based on the kinematic description.

24. The method of claim 23, wherein determining the insertion trajectory further based on the kinematic description comprises:
determining the insertion trajectory further based on a length of an end effector of the replacement tool relative to a length of the end effector of the previous tool.

25. The method of claim 23,
wherein the kinematic description of the replacement tool specifies a range of motion of a degree of freedom of the replacement tool, and
wherein determining the insertion trajectory further based on the kinematic description comprises:
determining the insertion trajectory further based on the range of motion of the degree of freedom of the replacement tool.

26. The method of claim 20, wherein controlling the replacement tool to move in accordance with the insertion trajectory comprises: controlling an end effector tip of the replacement tool to follow the insertion trajectory, and wherein the insertion trajectory comprises a curved section.

27. The method of claim 20, wherein determining the insertion trajectory based on the reference geometry comprises: reversing a removal trajectory of the previous tool.

28. The method of claim 20, further comprising:
facilitating a retraction of the replacement tool by controlling the replacement tool to move in accordance with a reversal of the insertion trajectory in response to the retraction of the replacement tool.

29. A non-transitory computer readable medium comprising a plurality of computer-readable instructions which, when executed by one or more processors associated with a medical system, are adapted to cause the one or more processors to perform a method comprising:
determining a kinematic configuration, the kinematic configuration being of a manipulator arm and a previous tool attached to the manipulator arm and with an end effector of the previous tool inserted at an insertion location;
determining a reference geometry of the previous tool in the kinematic configuration;
detecting a removal of the previous tool from the manipulator arm;
detecting an installation of a replacement tool on the manipulator arm;
determining a partially non-straight insertion trajectory for the replacement tool based on the reference geometry; and
controlling the replacement tool to move in accordance with the insertion trajectory while the replacement tool is inserted toward a target location of the insertion trajectory,
wherein the controlling the replacement tool to move in accordance with the insertion trajectory comprises controlling a joint of the replacement tool to alter an angle or position of the joint such that the end effector follows the partially non-straight insertion trajectory.

30. The non-transitory computer readable medium of claim 29, wherein the method further comprises:
impeding further insertion of the replacement tool past the target location; or
impeding movement of the replacement tool in response to the replacement tool reaching the target location.

31. The non-transitory computer readable medium of claim 29, wherein the controlling the replacement tool to move in accordance with the insertion trajectory results in an actuation of at least one degree of freedom of the manipulator arm other than an insertion degree of freedom.

32. The non-transitory computer readable medium of claim 29, wherein the method further comprises:
obtaining a kinematic description of the replacement tool; and
determining the insertion trajectory further based on the kinematic description.

33. The non-transitory computer readable medium of claim 32, wherein determining the insertion trajectory further based on the kinematic description comprises:
determining the insertion trajectory further based on a length of an end effector of the replacement tool relative to a length of the end effector of the previous tool; or
determining the insertion trajectory further based on a range of motion of a degree of freedom of the replacement tool.

34. The non-transitory computer readable medium of claim 29, wherein controlling the replacement tool to move in accordance with the insertion trajectory comprises: controlling an end effector tip of the replacement tool to follow the insertion trajectory, wherein the insertion trajectory comprises a curved section.

* * * * *

UNITED STATES PATENT AND TRADEMARK OFFICE
CERTIFICATE OF CORRECTION

Page 1 of 1

PATENT NO. : 12,128,566 B2
APPLICATION NO. : 17/438377
DATED : October 29, 2024
INVENTOR(S) : Ashwinram Suresh et al.

It is certified that error appears in the above-identified patent and that said Letters Patent is hereby corrected as shown below:

In the Claims

At Column 37, Claim number 20, Line numbers 24-25, "comprises the controlling is configured to: control" should read -- comprises: controlling --; and At Column 38, Claim number 29, Line number 29, "comprises" should read -- comprises: --.

Signed and Sealed this
Seventeenth Day of December, 2024

Derrick Brent
*Acting Director of the United States Patent and Trademark Office*